US007842245B2

(12) United States Patent
Ikeya et al.

(10) Patent No.: US 7,842,245 B2
(45) Date of Patent: Nov. 30, 2010

(54) FLUID HANDLING UNIT AND FLUID HANDLING APPARATUS USING SAME

(75) Inventors: Satoshi Ikeya, Saitama (JP); Kyouhei Yamada, Saitama (JP); Noriyuki Kawahara, Saitama (JP)

(73) Assignee: Enplas Corporation, Saitama (JP)

( * ) Notice: Subject to any disclaimer, the term of this patent is extended or adjusted under 35 U.S.C. 154(b) by 51 days.

(21) Appl. No.: 12/416,425

(22) Filed: Apr. 1, 2009

(65) Prior Publication Data

US 2009/0253196 A1 Oct. 8, 2009

(30) Foreign Application Priority Data

Apr. 4, 2008 (JP) ............................ 2008-098590

(51) Int. Cl.

| | |
|---|---|
| ***B01L 11/00*** | (2006.01) |
| ***B01L 3/00*** | (2006.01) |
| ***G01N 33/00*** | (2006.01) |
| ***C12M 1/34*** | (2006.01) |
| ***C12M 1/00*** | (2006.01) |

(52) U.S. Cl. ........................ 422/101; 422/68.1; 422/99; 422/102; 435/288.4; 435/288.5

(58) Field of Classification Search ....................... None
See application file for complete search history.

(56) References Cited

U.S. PATENT DOCUMENTS 4,623,461 A * 11/1986 Hossom et al. ............. 210/445
7,556,778 B2 * 7/2009 Kawahara et al. ........... 422/102
7,662,345 B2 * 2/2010 Kawahara et al. ........... 422/101
2005/0136546 A1 * 6/2005 Berndt et al. ................. 436/45
2007/0111304 A1 * 5/2007 Ohse et al. ............... 435/287.2
2008/0293129 A1 * 11/2008 Kawahara et al. ........ 435/287.2

FOREIGN PATENT DOCUMENTS

JP 9101302 A 4/1997
JP 9159673 A 6/1997
JP 2001-004628 A 1/2001

* cited by examiner

*Primary Examiner*—Jill Warden
*Assistant Examiner*—Charles Hammond
(74) *Attorney, Agent, or Firm*—Bachman & LaPointe, P.C.

(57) ABSTRACT

A fluid handling unit 16 has an inside cylindrical portion 16*c* which is arranged in an outside small-diameter cylindrical portion 16*b* so as to be eccentric with respect to the outside small-diameter cylindrical portion 16*b*, and a plurality of slits 16*d* for establishing a communication between an inside fluid housing chamber 30 and an outside fluid housing chamber 28. The most part of liquid in the inside fluid housing chamber 30 enters the outside fluid housing chamber 28, in which the height of the liquid level varies in circumferential directions, when the quantity of the fed liquid is not larger than a predetermined quantity. The liquid in the outside fluid housing chamber 28 enters the inside fluid housing chamber 30 when the quantity of the fed liquid exceeds the predetermined quantity.

23 Claims, 17 Drawing Sheets

FLUID HANDLING UNIT AND FLUID HANDLING APPARATUS USING SAME

BACKGROUND OF THE INVENTION

1. Field of the Invention

The present invention generally relates to a fluid handling unit and a fluid handling apparatus using the same. More specifically, the invention relates to a fluid handling unit capable of being used as a part of a sample analyzing apparatus for analyzing samples, such as biosubstances representative of functional substances, and a fluid handling apparatus using the same.

2. Description of the Prior Art

As conventional methods for specifically detecting biosubstances, such as proteins, there are known various methods for causing an antigen-antibody reaction using an antibody to a specific biosubstance, to carry out the visual recognition or spectroscopic measurement of a reactant thus obtained, to detect the biosubstance.

As methods for quantifying a reactant obtained by an antigen-antibody reaction of a biosubstance, such as a protein, there are widely adopted some methods, such as ELISA (Enzyme-Linked Immunosorbent Assay). In these methods, there is used a sample analyzing apparatus called a microplate wherein a large number of fine recessed portions generally called microwells (which will be hereinafter referred to as "wells") are arrayed. The wall surfaces of the wells are coated with an antibody to a specific biosubstance, which is a target substance, as a capturing (or catching) material, to capture (or catch) the target substance by the capturing material to detect the target substance by measuring a reactant, which is obtained by an antigen-antibody reaction between the target substance and the antibody, by fluorescence, luminous reagents or the like.

In a typical method using a microplate, such as ELISA, a well is filled with a liquid, such as a specimen containing a target substance or an antibody reagent, as a reaction solution to cause a reaction. This reaction does not occur until the components in the liquid filled in the well are moved by molecular diffusion to reach the bottom and inner walls of the well. For that reason, if a microplate is allowed to stand, a theoretical reaction time depends on the diffusion time of the components in the liquid filled in the well. Since the molecules in the liquid move while colliding with the surrounding molecules, the speed of diffusion is very slow. If the target substance is a protein having a molecular weight of about 70,000, the speed of diffusion is about 0.5 to $1\times10^{-6}$ $cm^2$/sec in a dilute aqueous solution (room temperature). Therefore, in the liquid filled in the well, the target substance located apart from the bottom and inner walls of the well is hardly allowed to react in a practical measuring time. In addition, since it is effective to cause the bottom and wall surfaces in the well serving as a reacting portion to uniformly contact the reaction solution in order to improve the efficiency of reaction in a microplate, it is required to use a larger quantity of liquid than the quantity of liquid required for the reaction.

Thus, in the conventional method using the microplate, such as ELISA, the antigen-antibody reaction proceeds only on the wall surface of the well coated with the capturing antibody. Therefore, the liquid must be allowed to stand until the reaction occurs after the target substance, antibody and substrate contained in the liquid fed into the well are suspended, circulated and sink to reach the wall surface of the well, so that there is a problem in that the efficiency of reaction is bad. In addition, in a microplate which is subdivided into a large number of wells, the quantity of liquid fed into each of the wells is limited, so that there is a problem in that the sensitivity of measurement is deteriorated.

In order to improve the sensitivity of measurement and shorten the measuring time in ELISA or the like, there is proposed a microplate capable of increasing the surface area of a reaction surface (capturing surface) to enhance the sensitivity of measurement by forming fine irregularities on the bottom face of each of wells serving as the reaction surface (see, e.g., Japanese Patent Laid-Open No. 9-159673). There is also proposed a microchip capable of increasing the surface area of a reaction surface to enhance the efficiency of reaction in a fine space by arranging a fine solid particle (bead) as a reaction solid phase in a microchannel of the microchip (see, e.g., Japanese Patent Laid-Open No. 2001-4628). Moreover, there is proposed a microplate capable of increasing the surface area of a reaction surface and saving the quantity of samples by forming a small-diameter recessed portion in the central portion of the bottom of each of wells. (see, e.g., Japanese Patent Laid-Open No. 9-101302).

However, in the microplate proposed in Japanese Patent Laid-Open No. 9-159673, there is a problem in that it is not possible to improve the efficiency of reaction although it is possible to improve the sensitivity of measurement. In addition, the microchip proposed in Japanese Patent Laid-Open No. 2001-4628 is not suitable for the measurement of a large number of specimens although it is possible to improve the efficiency of reaction, since it is a microchip having a microchannel structure, not a microplate typically used in ELISA or the like. Moreover, in the microplate proposed in Japanese Patent Laid-Open No. 9-101302, it is not possible to sufficiently improve the efficiency of reaction and the sensitivity of measurement, although it is possible to increase the surface area of the reaction surface to improve the efficiency of reaction and the sensitivity of measurement to some extent.

In addition, it is desired to provide a fluid handling apparatus capable of further improving the accuracy of analysis even if the quantity of a reagent or specimen for use in analysis is very small. It is also desired to allow the interior of such an apparatus to be easily and sufficiently cleaned to lower background during measurement to further improve the accuracy of analysis.

SUMMARY OF THE INVENTION

It is therefore an object of the present invention to eliminate the aforementioned problems and to provide a fluid handling unit for use in a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling apparatus using the same.

It is another object of the present invention to allow the above-described fluid handling unit or fluid handling apparatus using the same to further improve the accuracy of analysis even if the quantity of a reagent or specimen for use in analysis is very small, and to allow the interior of the fluid handling unit or fluid handling apparatus to be easily and sufficiently cleaned.

In order to accomplish the aforementioned and other objects, according to one aspect of the present invention, a fluid handling unit comprises: an container body having an opening at an upper end thereof, a bottom portion at a lower end thereof, and a side portion which extends from a peripheral portion of an upper face of the bottom portion, the container body defining therein a fluid housing section by the bottom portion and the side portion; a partition wall portion which extends from the bottom portion of the container body and which extends along the side portion of the container body, the partition wall portion dividing the fluid housing section of the container body into an inside fluid housing chamber and an outside fluid housing chamber which surrounds the inside fluid housing chamber; and a communication passage which passes through the partition wall portion to establish a communication between the inside fluid housing chamber and the outside fluid housing chamber, wherein a distance between the side portion of the container body and the partition wall portion varies in circumferential directions for changing a capillary force, which is exerted on a liquid housed in the outside fluid housing chamber, in the circumferential directions which extend along the peripheral portion of the upper face of the bottom portion of the container body.

In this fluid handling unit, the distance between the side portion of the container body and the partition wall portion may gradually vary in the circumferential directions so that the liquid housed in the outside fluid housing chamber flows in the circumferential directions by the capillary force. The liquid housed in the outside fluid housing chamber may flow in the circumferential directions by the capillary force from a wider portion, in which the distance between the side portion of the container body and the partition wall portion is wider, toward a narrower portion in which the distance between the side portion of the container body and the partition wall portion is narrower. The distance between the side portion of the container body and the partition wall portion may be substantially uniform in directions perpendicular to the circumferential directions. The side portion of the container body may have a substantially cylindrical inside face, and the partition wall portion may have a substantially cylindrical outside face which is eccentrically arranged in radial directions with respect to the inner face of the side portion of the container body. Alternatively, the side portion of the container body may have a substantially cylindrical inside face, and the partition wall portion may have a substantially elliptic cylindrical outside face.

In the above-described fluid handling unit, the communication passage may comprise a plurality of slits which pass through the partition wall portion and which extend from a lower end of the partition wall portion to an upper end thereof. In this case, the plurality of slits may be arranged at regular intervals in the circumferential directions. Alternatively, the plurality of slits may be arranged substantially in parallel, and a nozzle housing portion may be formed so as to pass through the partition wall portion to extend substantially in parallel to the plurality of slits from the lower end of the partition wall portion to the upper end thereof, the nozzle housing portion being capable of housing therein a suction nozzle for sucking a fluid flowing in the circumferential directions into a narrower portion, in which the distance between the side portion of the container body and the partition wall portion is narrower, from a wider portion in which the distance between the side portion of the container body and the partition wall portion is wider.

In the above-described fluid handling unit, a liquid in the inside fluid housing chamber may be caused to enter the outside fluid housing chamber due to capillarity while being prevented from entering the inside fluid housing chamber when the quantity of the liquid fed into the fluid housing section from the opening of the container body is not larger than a predetermined quantity, and the liquid in the outside fluid housing chamber may be allowed to enter the inside fluid housing chamber when the quantity of the liquid fed to the fluid housing section from the opening of the container body exceeds the predetermined quantity. In this case, the most part of the liquid in the inside fluid housing chamber may enter the outside fluid housing chamber when the quantity of the liquid fed into the fluid housing section from the opening of the container body is not larger than the predetermined quantity.

In the above-described fluid handling unit, the communication passage may cause the liquid in the inside fluid housing chamber to enter the outside fluid housing chamber while preventing the liquid in the outside fluid housing chamber from entering the inside fluid housing chamber, by a difference between a capillary force exerted in the inside fluid housing chamber and a capillary force exerted in the outside fluid housing chamber, when the quantity of the liquid fed into the fluid housing section from the opening of the container body is not larger than a predetermined quantity. In this case, the capillary force exerted in the outside fluid housing chamber may be greater than the capillary force exerted in the inside fluid housing chamber.

In the above-described fluid handling unit, the partition wall portion may have a height which is lower than that of the side portion of the container body. The bottom portion of the outside fluid housing chamber may be inclined downwards as a distance from the inside fluid housing chamber decreases. The height of the lowest portion of the bottom portion of the outside fluid housing chamber may be substantially equal to the height of that of the inside fluid housing chamber. The width of each of the slits on the side of the inside fluid housing chamber may be longer than that on the side of the outside fluid housing chamber. The fluid handling unit may be integral-molded.

According to another aspect of the present invention, a fluid handling apparatus comprises: an apparatus body; and a plurality of fluid handling units arranged on the apparatus body, wherein each of the plurality of fluid handling units is the above-described fluid handling unit. In this fluid handling apparatus, the plurality of fluid handling units may be arranged on the apparatus body as a matrix. The plurality of fluid handling units, together with the apparatus body, may be integral-molded. Alternatively, the apparatus body may comprise a frame and a plurality of supporting members arranged on the frame substantially in parallel, and the plurality of fluid handling units may be arranged on each of the supporting members at regular intervals in a row. In this case, the plurality of fluid handling units, together with each of the supporting member, may be integral-molded.

According to the present invention, it is possible to provide a fluid handling unit which is capable of improving the efficiency of reaction and the sensitivity of measurement with a simple structure and of shortening a reaction time and a measuring time, and a fluid handling apparatus using the same, when the apparatus is used as a sample analyzing apparatus for measuring a large number of specimens.

According to the present invention, it is also possible to allow the fluid handling unit or fluid handling apparatus using the same to further improve the accuracy of analysis even if the quantity of a reagent or specimen for use in analysis is very small, and to allow the interior of the fluid handling unit or fluid handling apparatus to be easily and sufficiently cleaned.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a fluid handling unit and a fluid handling apparatus using the same according to the present invention will be described below in detail.

Figure 1:
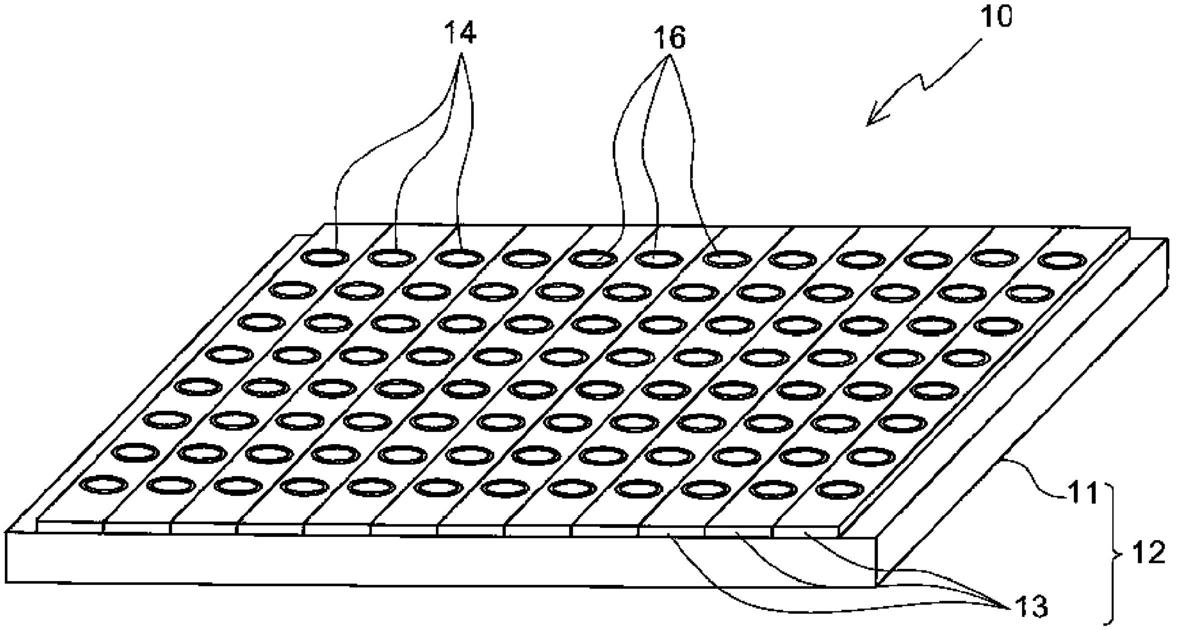
FIG. 1 is a perspective view of the preferred embodiment of a fluid handling apparatus according to the present invention.

FIGS. 1 through 10 show the preferred embodiment of a fluid handling unit and a fluid handling apparatus according to the present invention. For example, the fluid handling apparatus 10 in this preferred embodiment can be used as an apparatus for analyzing a sample containing a biosubstance, such as a protein, which is representative of functional substances. In general, the fluid handling apparatus 10 can be used as a sample analyzing apparatus called a microwell plate for carrying out the measurement of a large number of specimens. As shown in FIG. 1, the fluid handling apparatus 10 comprises: an apparatus body 12; and a plurality of fluid handling units 16 (96(=8×12) fluid handling units in this preferred embodiment) mounted on the apparatus body 12 so as to be arranged as a matrix.

Figure 2:
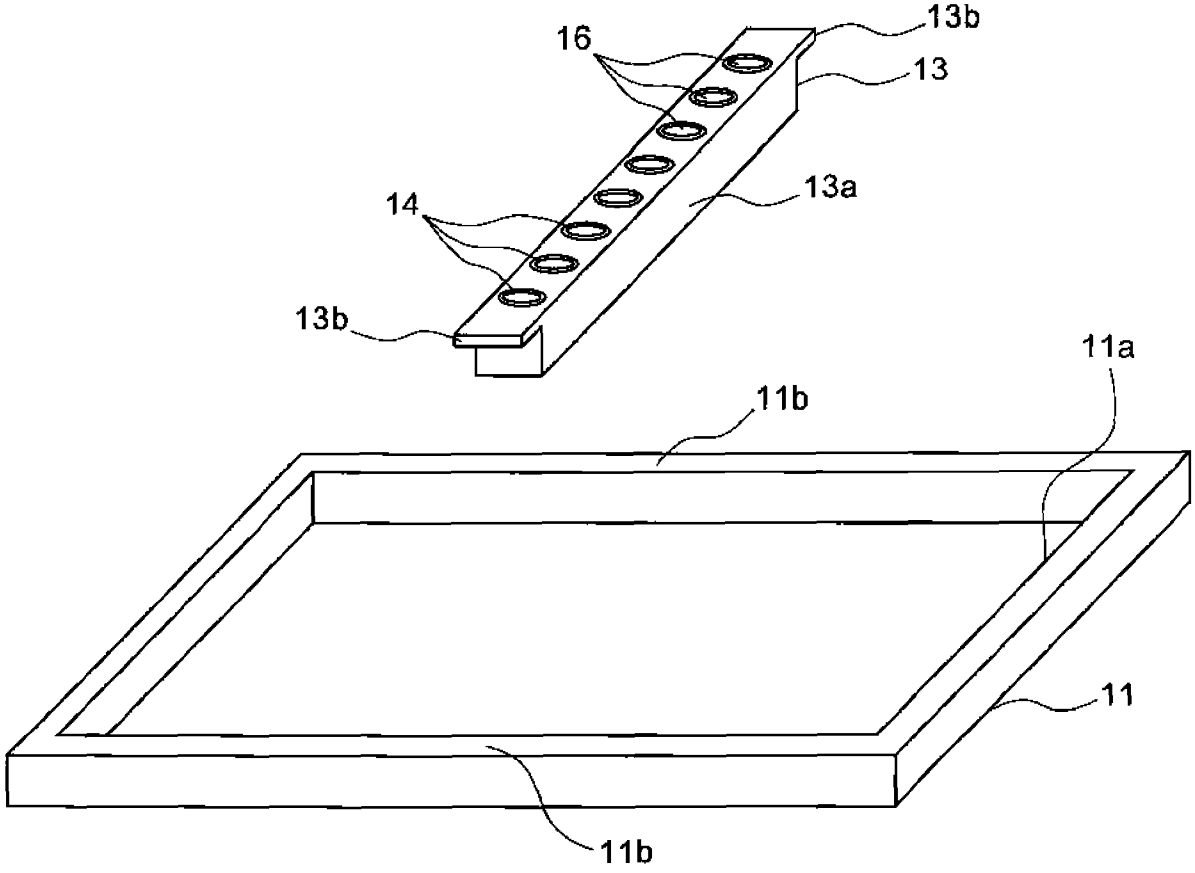
FIG. 2 is a perspective view showing a frame and a fluid handling unit supporting member of the apparatus body of the fluid handling apparatus of FIG. 1.

As shown in FIGS. 1 and 2, the apparatus body 12 is made of a resin material, such as polystyrene (PS), polycarbonate (PC) or polymethyl methacrylate (PMMA), or a glass material, and comprises: a substantially rectangular frame 11 which has a substantially rectangular through hole 11*a* in the center thereof and which has a thickness of a few millimeters, the length of each side of the frame 11 being in the range of from a few centimeters to over ten centimeters; and a plurality of fluid handling unit supporting members 13 (12 fluid handling unit supporting members in this preferred embodiment) mounted on the frame 11. Furthermore, the through hole 11*a* of the frame 11 may be replaced with a recessed portion with bottom. Alternatively, the frame 11 may be a standard frame, such as a frame for microplate of SBS (Society for Biomolecular Screening) standard. The fluid handling unit supporting members 13 may be made of a transparent material. However, if the fluid handling apparatus 10 in this preferred embodiment is used for measuring fluorescence, the fluid handling unit supporting members 13 are preferably made of a member (e.g., a black member) which is difficult to allow light to pass through the member in order to suppress the rise of background during the measurement of fluorescence.

As shown in FIG. 2, each of the fluid handling unit supporting members 13 comprises: an elongated supporting member body 13*a* having a shape of substantially rectangular parallelepiped, the length of which is substantially equal to the width of the through hole 11*a* of the frame 11; and a pair of substantially rectangular protruding portions 13*b* which protrude from the upper portions of the supporting member body 13*a* at both ends in longitudinal directions to extend along the upper surface of the supporting member body 13*a*. As shown in FIG. 1, the supporting member bodies 13*a* of the fluid handling unit supporting members 13 are inserted into the through hole 11*a* of the frame 11 to be mounted on the frame 11 substantially in parallel and adjacent to each other so that the protruding portions 13*b* are supported on a pair of upper surfaces 11*b* of the frame 11 extending in longitudinal directions. Thus, the apparatus body 12 is assembled.

Figure 3:
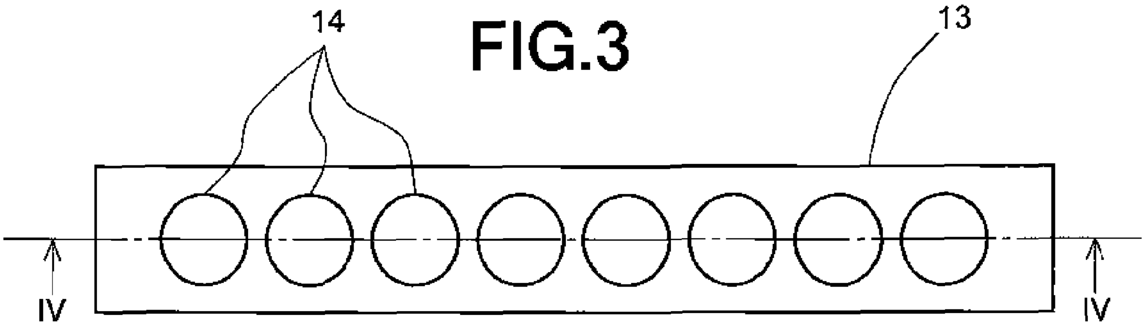
FIG. 3 is an enlarged plan view of the fluid handling unit supporting member of FIG. 2.
Figure 4:
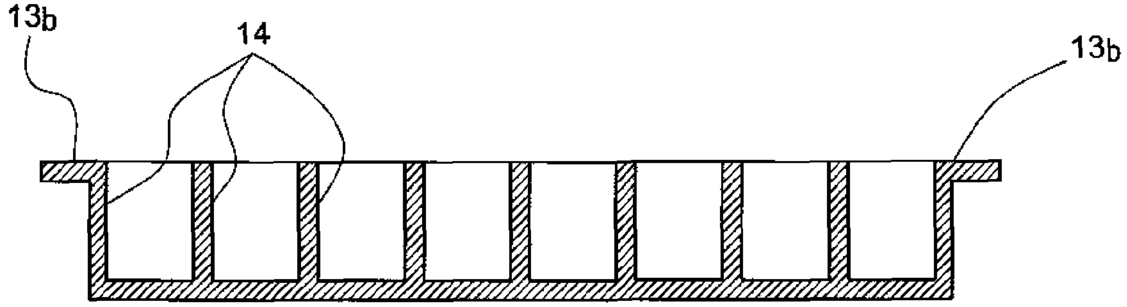
FIG. 4 is a sectional view taken along line IV-IV of FIG. 3.
Figure 5:
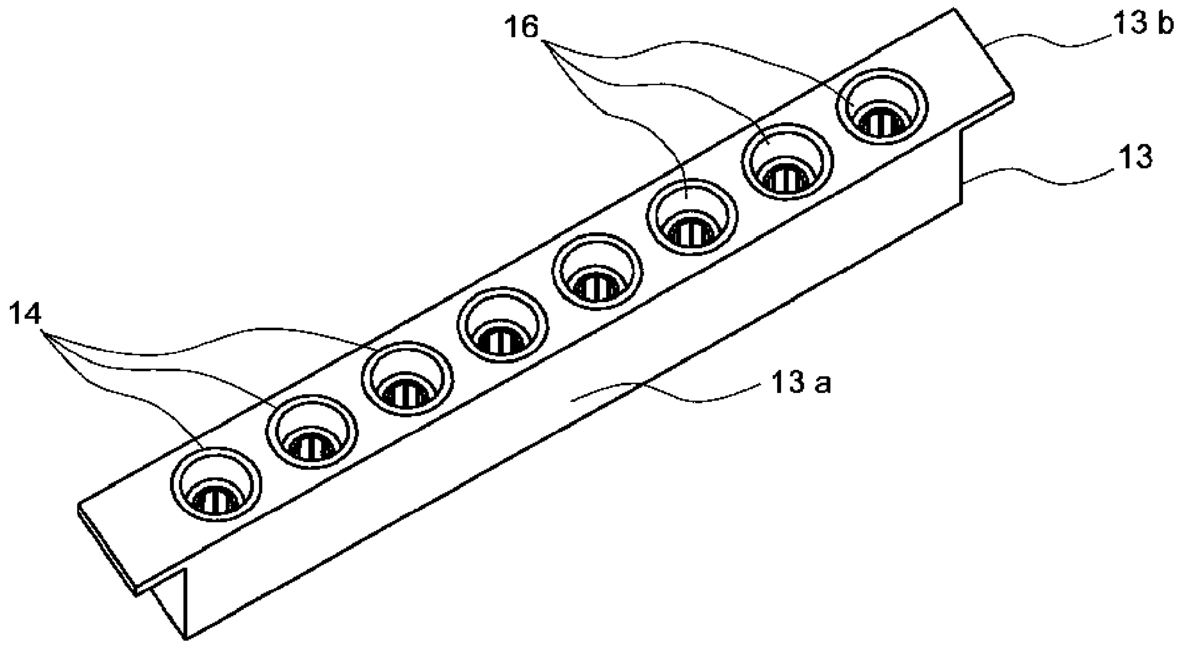
FIG. 5 is a perspective view showing a state that fluid handling units are mounted on the fluid handling unit supporting member of FIG. 2.

As shown in FIGS. 3 and 4, a plurality of substantially cylindrical recessed portions 14 (eighth recessed portions 14 in this preferred embodiment) (which will be hereinafter referred to as "mounting recessed portions 14") having a diameter and depth of a few millimeters are formed in the upper surface of the supporting member body 13*a* of each of the fluid handling unit supporting members 13 so as to be arranged at regular intervals in a row. In each of the mounting recessed portions 14, one of the fluid handling units 16 is mounted as shown in FIG. 5.

Figure 6:
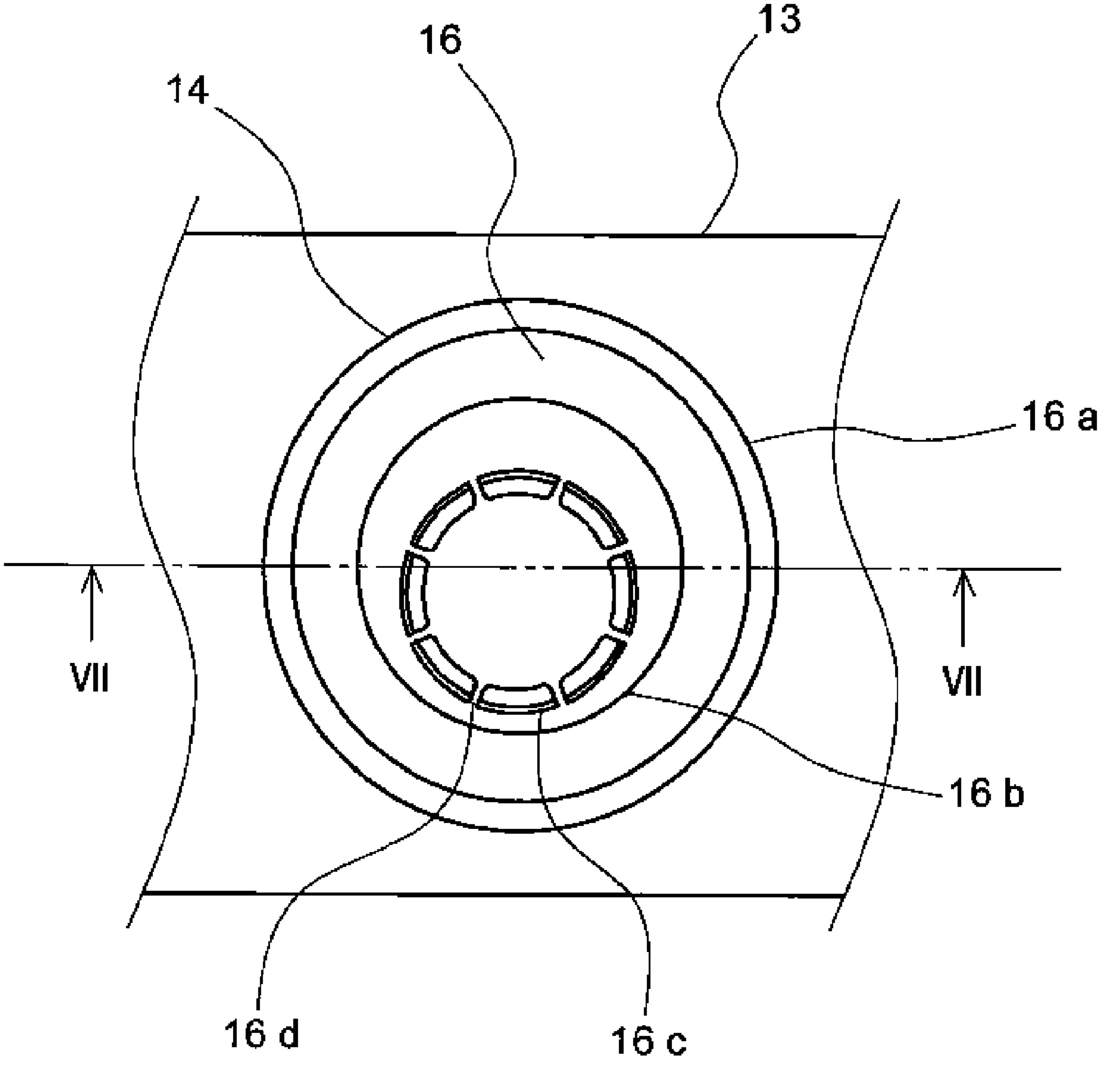
FIG. 6 is an enlarged plan view of one of the fluid handling units, each of which is mounted in corresponding one of mounding recessed portions of the fluid handling apparatus of FIG. 1.
Figure 7:
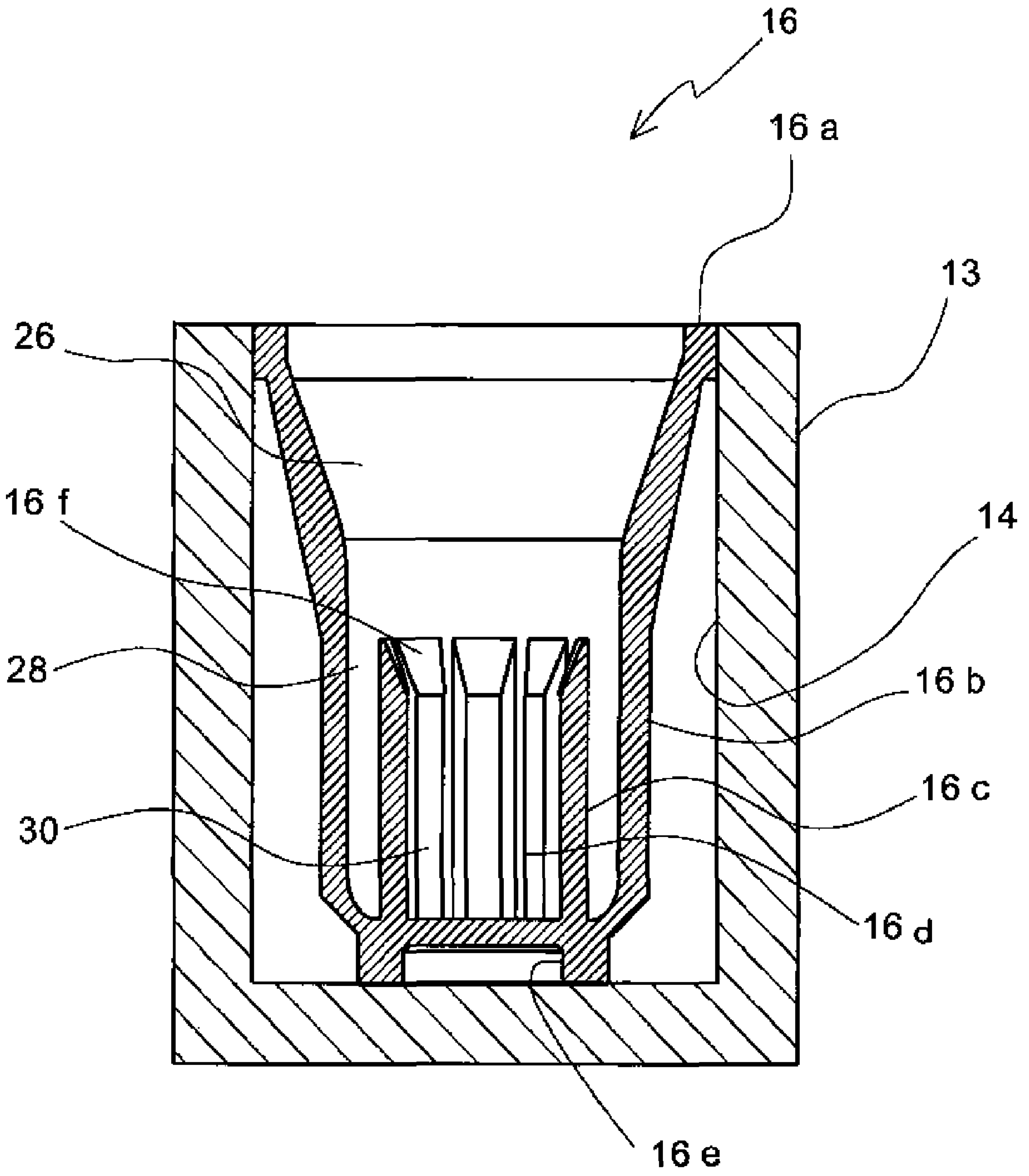
FIG. 7 is a sectional view taken along line VII-VII of FIG. 6.
Figure 8A:
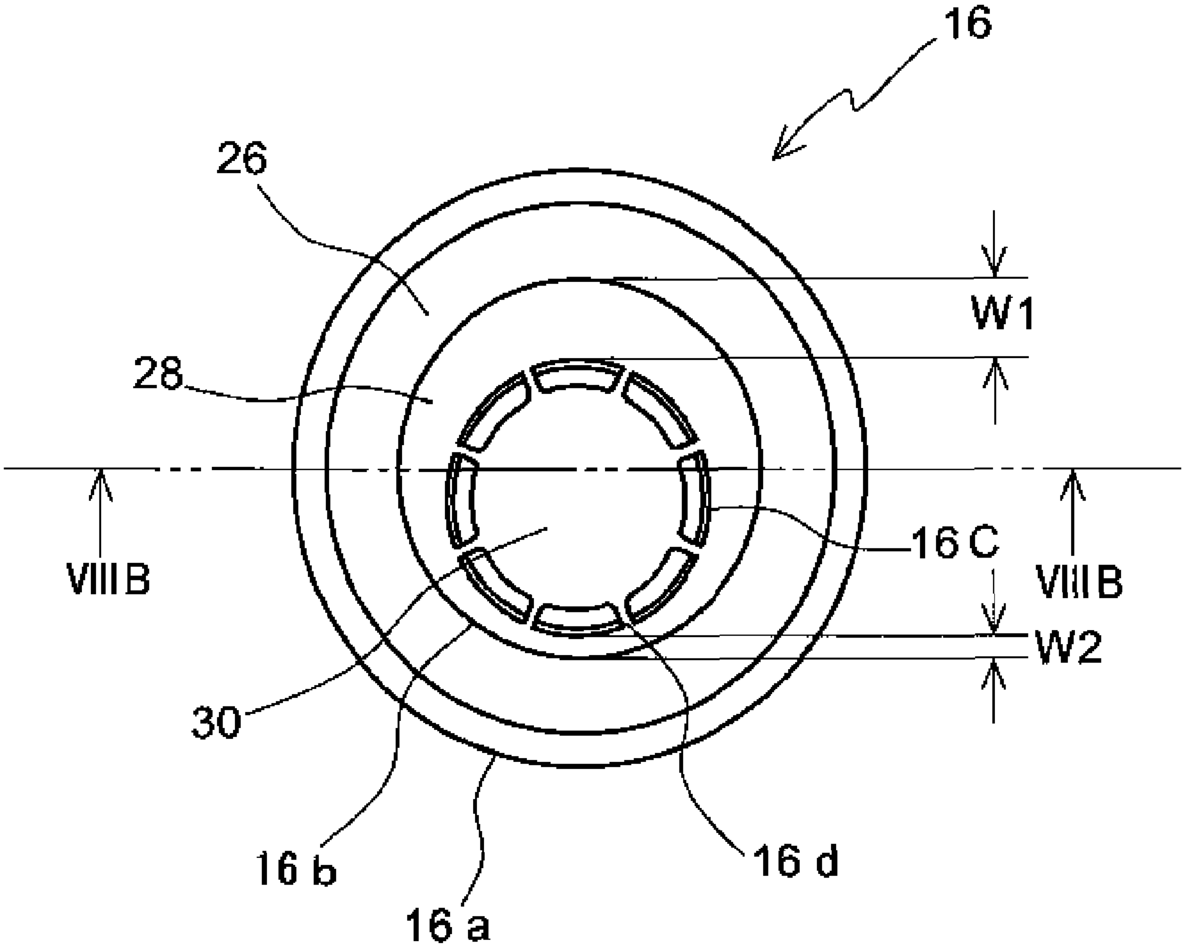
FIG. 8A is an enlarged plan view of one of the fluid handling units of the fluid handling apparatus of FIG. 1.
Figure 8B:
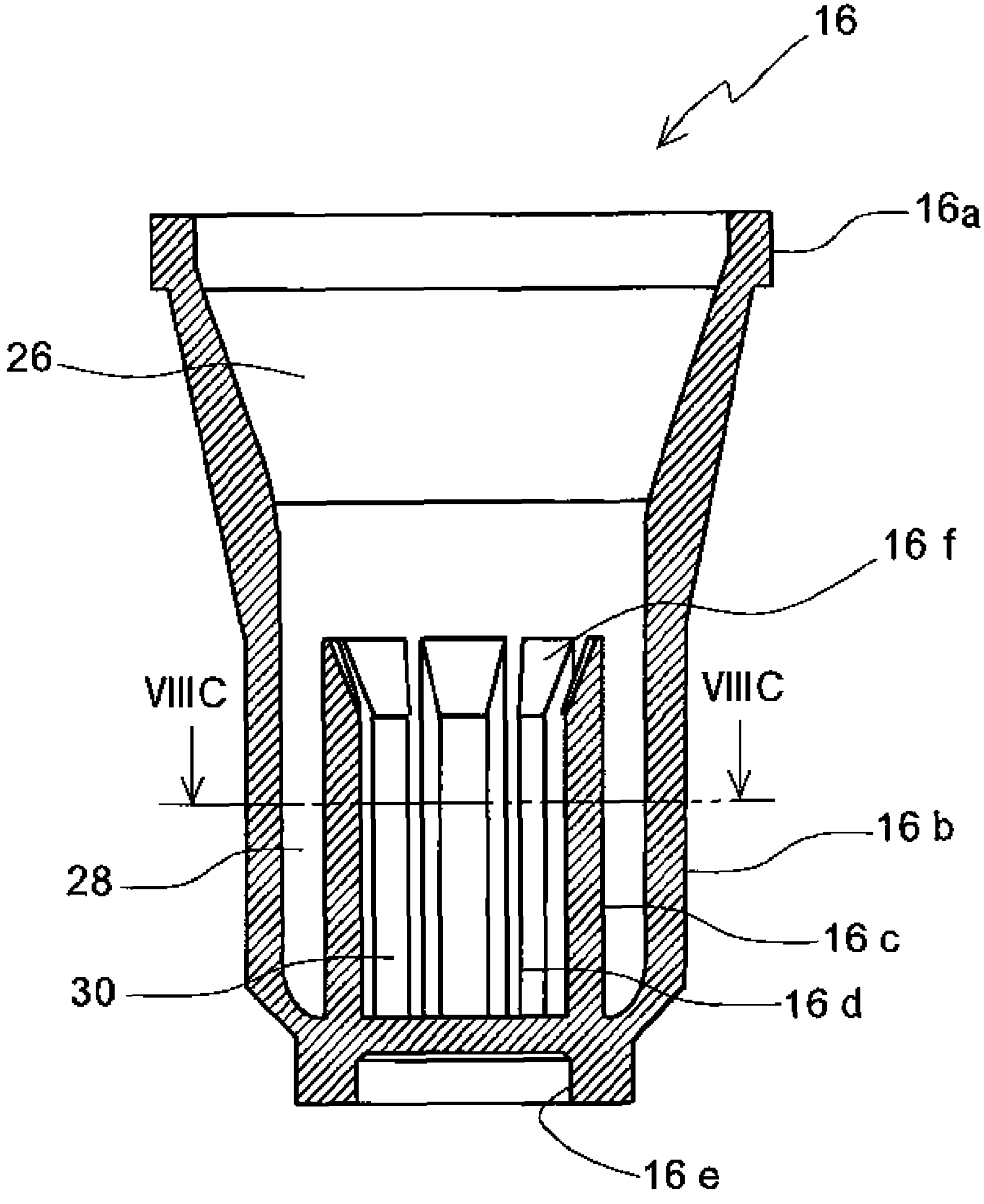
FIG. 8B is a sectional view taken along line VIIIB-VIIIB of FIG. 8A.
Figure 8C:
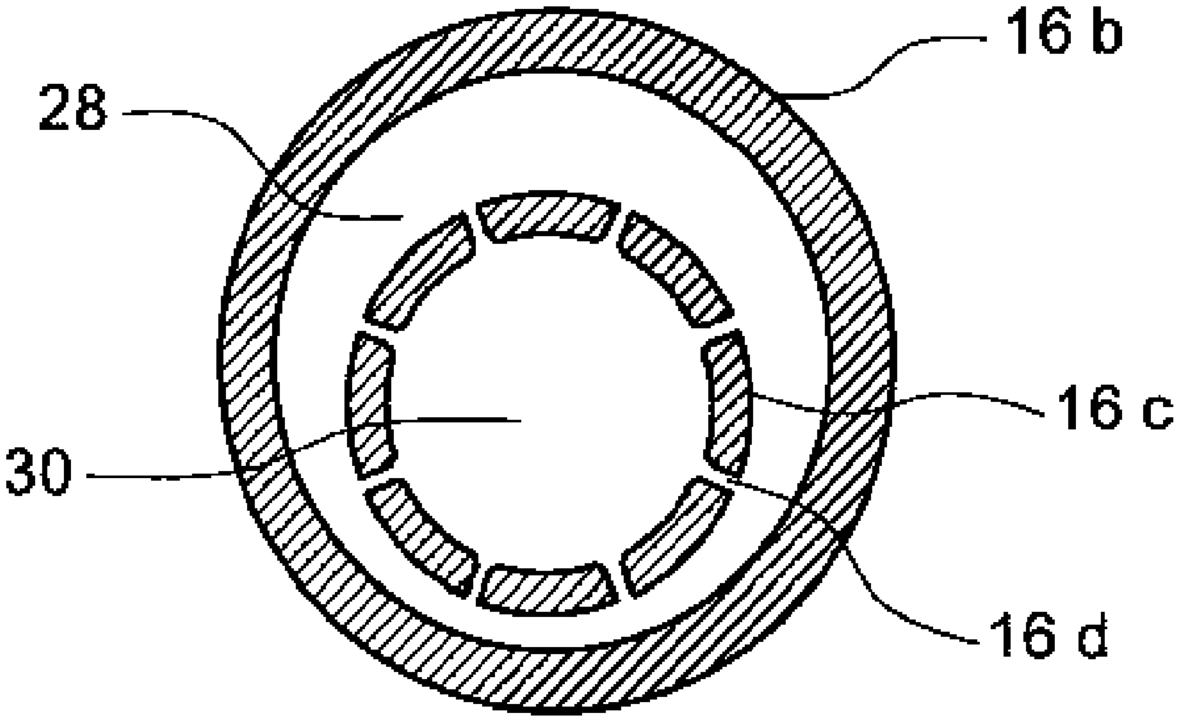
FIG. 8C is a sectional view taken along line VIIIC-VIIIC of FIG. 8B.
Figure 8D:
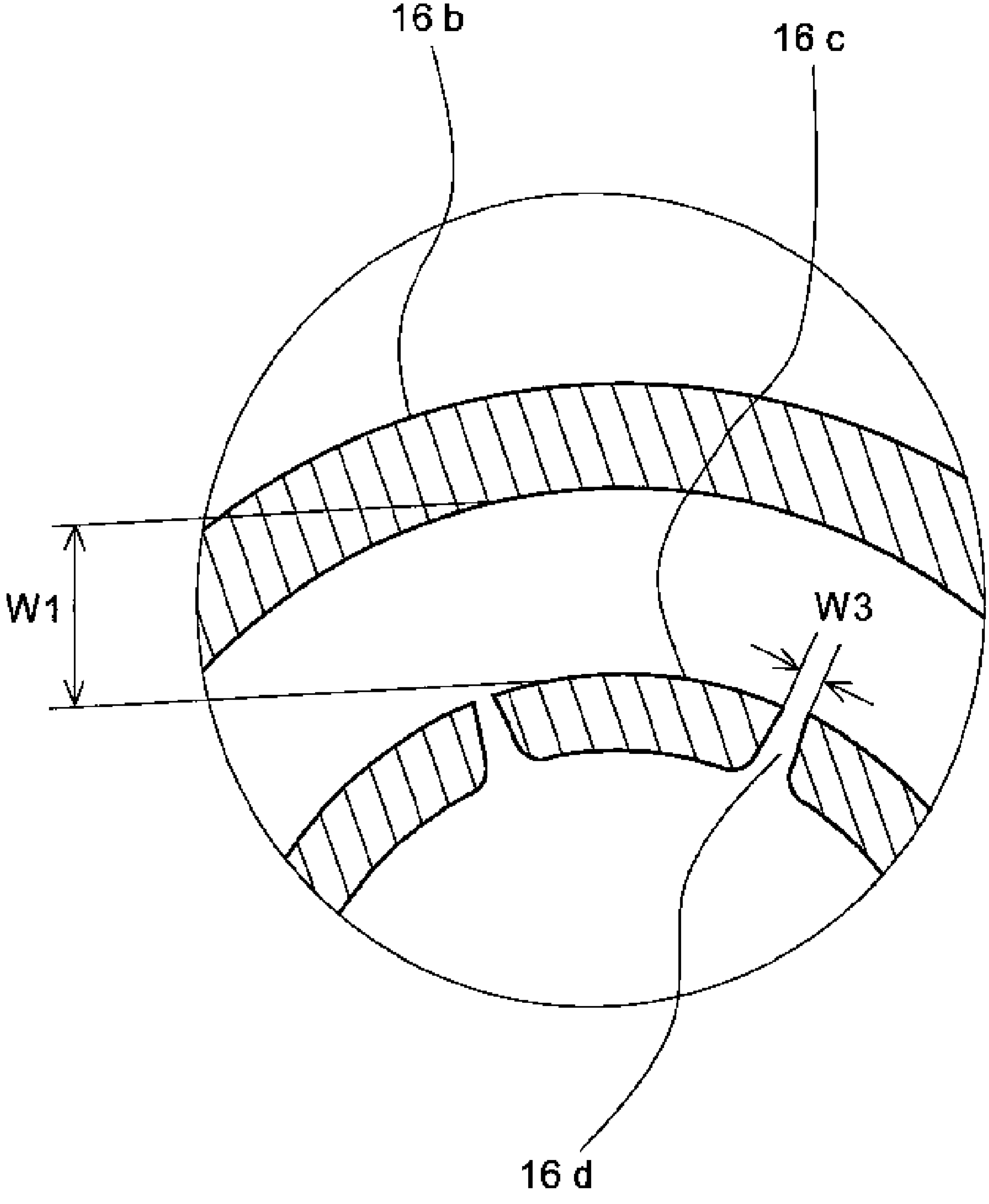
FIG. 8D is an enlarged view of a part of FIG. 8C.
Figure 9A:
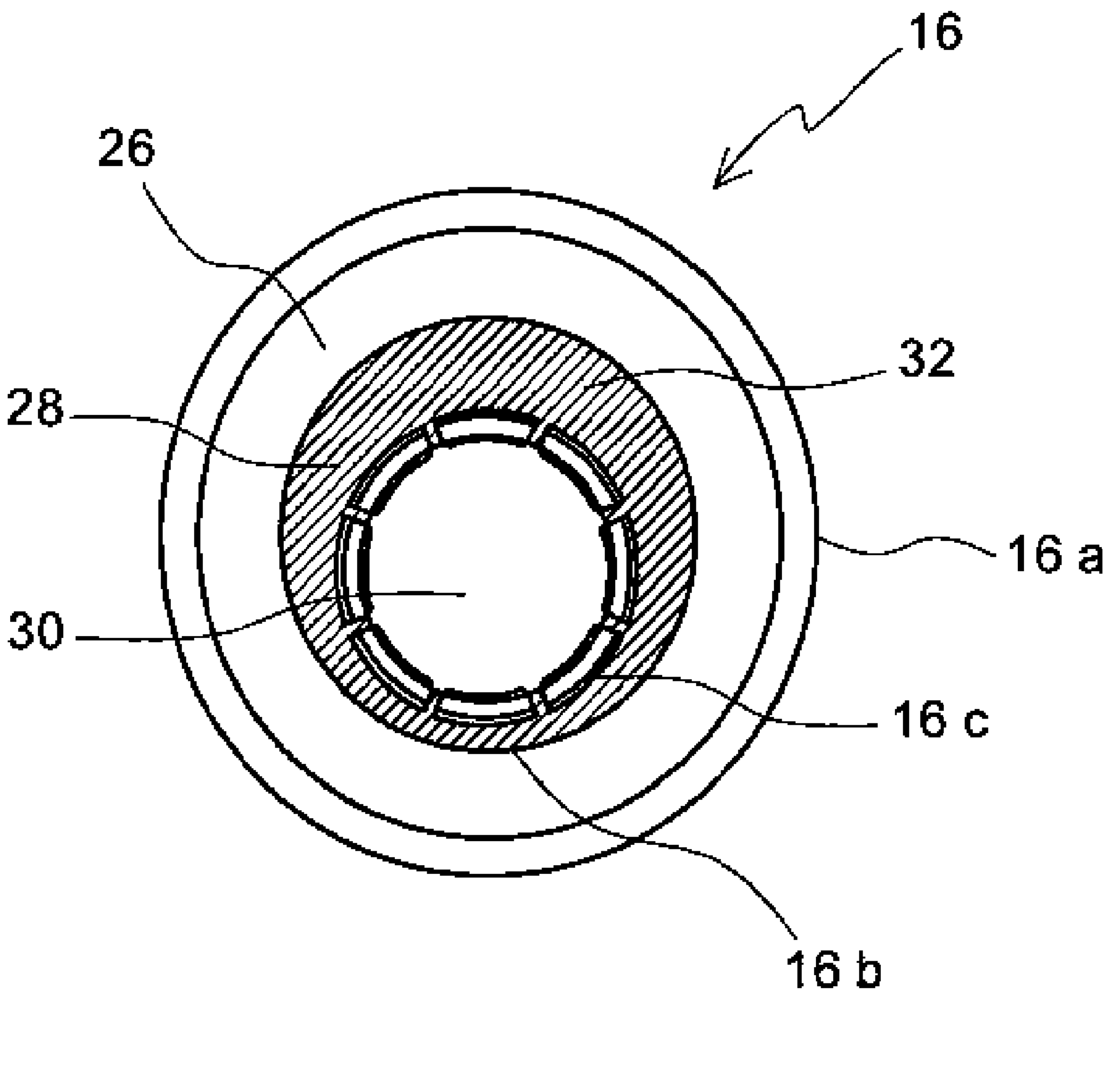
FIG. 9A is an enlarged plan view showing a state that a small quantity of liquid is fed into the preferred embodiment of the fluid handling unit according to the present invention, which corresponds to FIG. 8A.
Figure 9B:
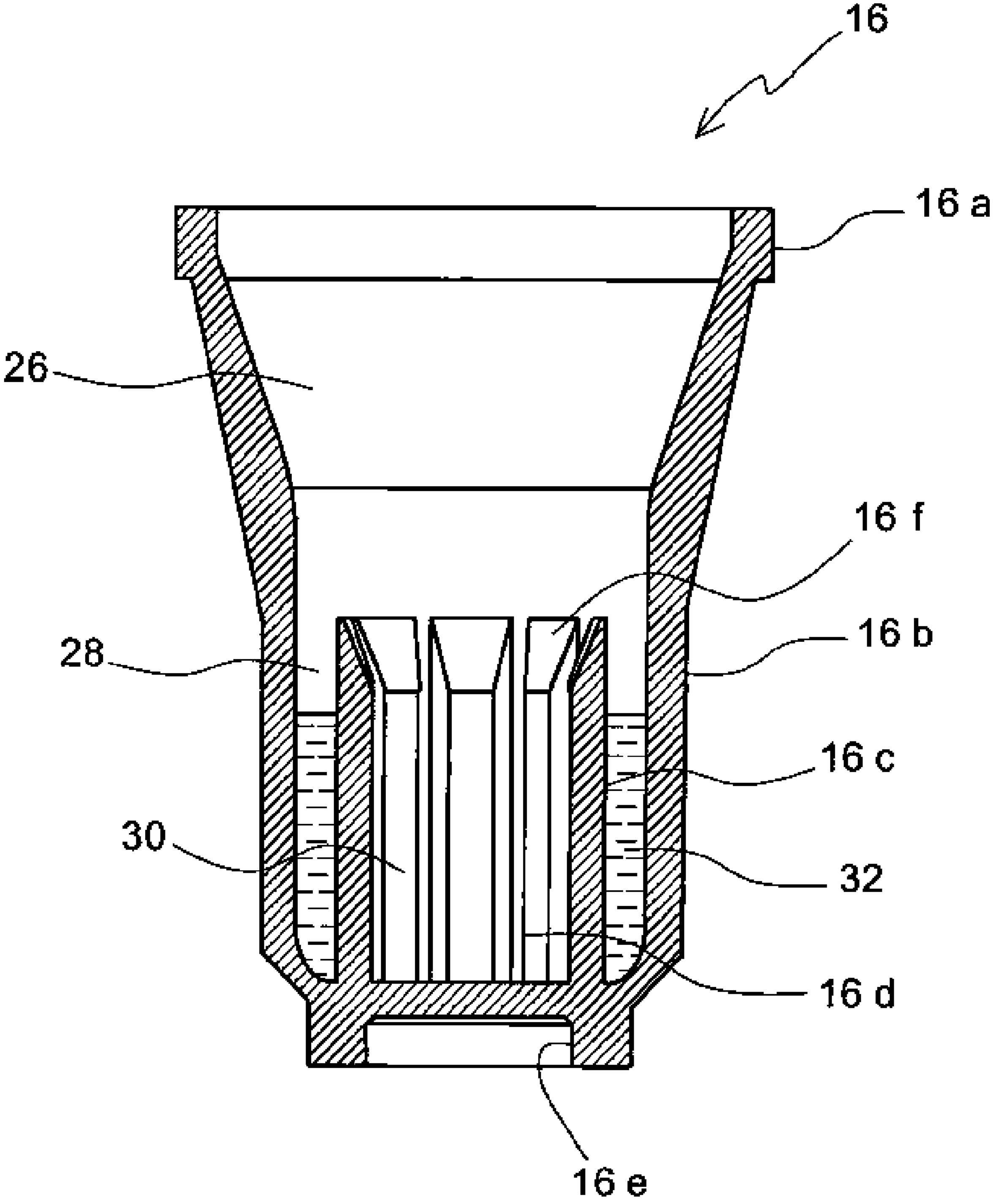
FIG. 9B is a sectional view showing a state that a small quantity of liquid is fed into the preferred embodiment of the fluid handling unit according to the present invention, which corresponds to FIG. 8B.
Figure 10:
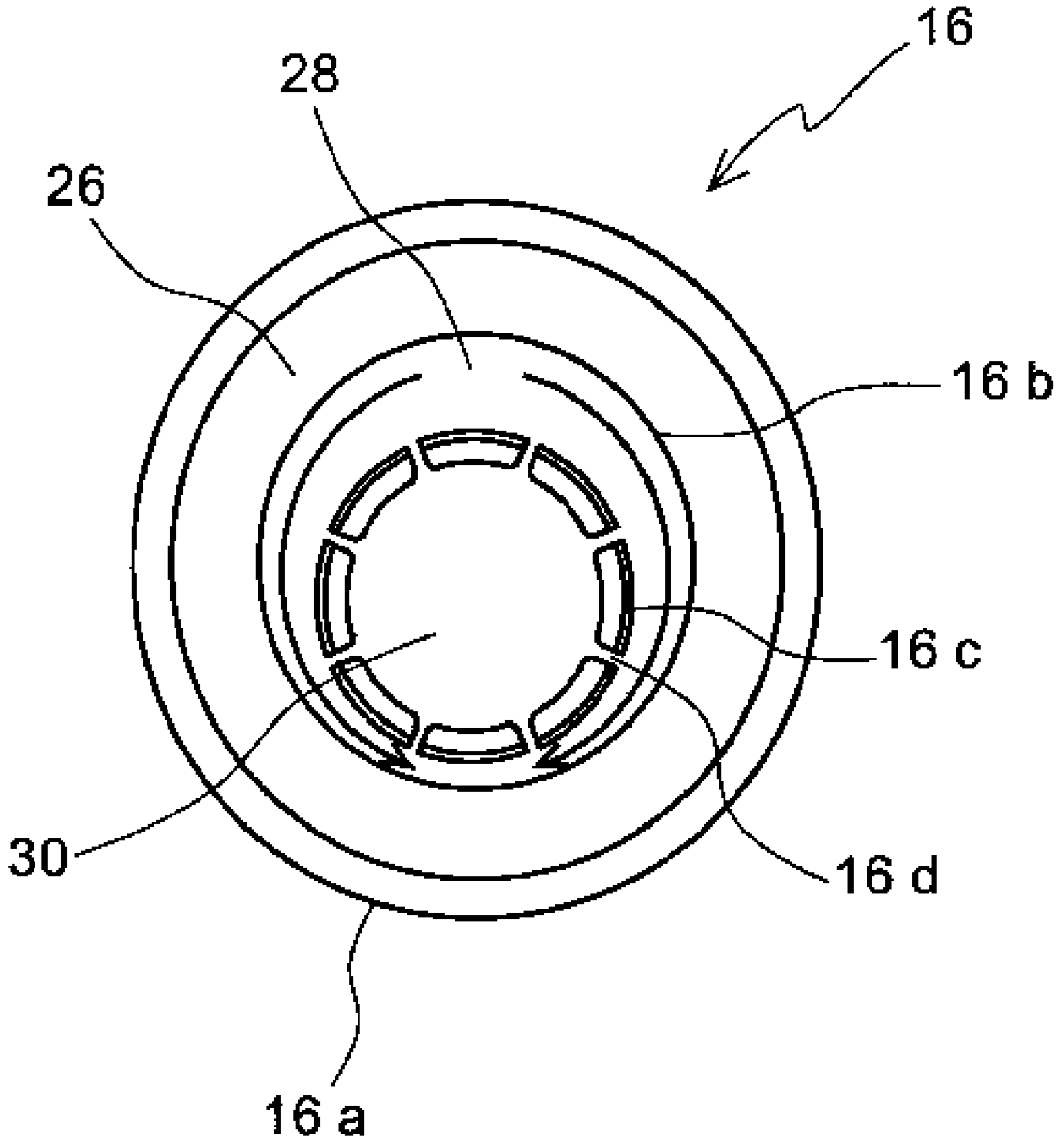
FIG. 10 is an enlarged plan view showing the flow of a small quantity of liquid existing in the preferred embodiment of the fluid handling unit according to the present invention.

FIGS. 6 through 10 are enlarged views showing one of the fluid handling units 16, each of which is mounted in a corresponding one of the mounting recessed portions 14 of the fluid handling apparatus 10 in this preferred embodiment. FIG. 6 is a plan view of one of the fluid handling units 16, each of which is mounted in a corresponding one of the mounting recessed portions 14 of the fluid handling apparatus 10, and FIG. 7 is a sectional view taken along line VII-VII of FIG. 6. FIG. 8A is a plan view of one of the fluid handling units 16 of the fluid handling apparatus 10 in this preferred embodiment, and FIG. 8B is a sectional view taken along line VIIIB-VIIIB of FIG. 8A. FIG. 8C is a sectional view taken along line VIIIC-VIIIC of FIG. 8B, and FIG. 8D is an enlarged view of a part of FIG. 8C. FIGS. 9A and 9B show a state that a small quantity of liquid is fed into the fluid handling unit 16, FIG. 9A being a plan view corresponding to FIG. 8A, and FIG. 9B being a sectional view corresponding to FIG. 8B. FIG. 10 is an enlarged plan view showing the flow of a small quantity of liquid existing in the fluid handling unit 16.

Each of the fluid handling units 16 is made of a resin material, such as polystyrene (PS), polycarbonate (PC) or polymethyl methacrylate (PMMA). As shown in FIGS. 6 through 8B, each of the fluid handling units 16 substantially has the same height as the depth of the corresponding one of the mounting recessed portions 14, and comprises an outside large-diameter cylindrical portion 16*a*, an outside small-diameter cylindrical portion 16*b* and an inside cylindrical portion 16*c* which are integral-molded so as to be integrated with each other.

The upper portion of the outside large-diameter cylindrical portion 16*a* is a substantially cylindrical portion which has an outside diameter being substantially equal to the inside diameter of the corresponding one of the mounting recessed portions 14. The upper portion of the outside large-diameter cylindrical portion 16*a* is designed to be fitted into the corresponding one of the mounting recessed portions 14 to be fixed thereto when each of the fluid handling units 16 is inserted into the corresponding one of the mounting recessed portions 14 to be mounted therein. The lower portion of the outside large-diameter cylindrical portion 16*a* is inclined inwardly downwards to extend to the outside small-diameter cylindrical portion 16*b* to be connected to the upper end portion of the outside small-diameter cylindrical portion 16*b*.

The outside small-diameter cylindrical portion 16*b* is a substantially cylindrical portion which has a smaller outside diameter than that of the outside large-diameter cylindrical portion 16*a*. The outside small-diameter cylindrical portion 16*b* extends in the same axial directions as those of the outer large-diameter cylindrical portion 16*a*. The lower portion of the outside small-diameter cylindrical portion 16*b* has a portion inclined inwardly downwards. From the bottom end of this portion inclined inwardly downwards, a bottom face portion extends in directions substantially perpendicular to the axial directions of the outside small-diameter cylindrical portion 16*b*. The underside of the bottom face portion of the outside small-diameter cylindrical portion 16*b* has a recessed portion 16*e* having a diameter which is substantially equal to the inside diameter of the inside cylindrical portion 16*c*.

The inside cylindrical portion 16*c* is a substantially cylindrical portion which extends upwards in the same axial directions as those of the outside small-diameter cylindrical portion 16*b* from the upper face of the bottom face portion of the outside small-diameter cylindrical portion 16*b*. The height of the upper end of the inside cylindrical portion 16*c* is lower than the upper portion of the outside small-diameter cylindrical portion 16*b*, and the outside diameter of the inside cylindrical portion 16*c* is smaller than the inside diameter of the outside small-diameter cylindrical portion 16*b*. The central axis of the inside cylindrical portion 16*c* is offset from the central axis of the outside small-diameter cylindrical portion 16*b* in a radial direction. That is, the inside cylindrical portion 16*c* is eccentrically arranged in radial directions with respect to the outside small-diameter cylindrical portion 16*b*. The inside cylindrical portion 16*c* has a plurality of slits 16*d* (eight slits 16*d* in this preferred embodiment) which extend substantially linearly in substantially parallel to each other from the bottom end of the inside cylindrical portion 16*c* to the upper end thereof. The plurality of slits 16*d* pass through the inside cylindrical portion 16*c*, and are arranged at regular intervals in circumferential directions thereof. That is, the inside cylindrical portion 16*c* comprises eight pillars which substantially have the same shape and which are spaced from each other so as to form the eight slits 16*d*. The width of each of the slits 16*d* is a few micrometers to hundreds micrometers, and the width of each of the slits 16*d* on the side of the inside face of the inside cylindrical portion 16*c* is longer than that on the side of the outside face thereof. The upper end face of the inside cylindrical portion 16*c* is an inclined surface 16*f* which is inclined inwardly downwards.

Furthermore, in the outside large-diameter cylindrical portion 16*a*, a space serving as an injecting section 26 for injecting a fluid, such as a liquid sample, is formed. Between the outside small-diameter cylindrical portion 16*b* and the inside cylindrical portion 16*c*, there is formed an outside fluid housing chamber 28 (having a volume of, e.g., not larger than about 30 μl) which is an annular space (having a bottom face inclined inwardly downwards) capable of being used as a reaction chamber. In the inner cylindrical portion 16*c*, there is formed an inside fluid housing chamber 30 which is a substantially cylindrical chamber capable of being used as a measuring chamber Furthermore, since the inside cylindrical portion 16*c* is eccentrically arranged in radial directions with respect to the outside small-diameter cylindrical portion 16*b* as described above, the width of the annular outside fluid housing chamber 28 in radial directions (the distance between the outside small-diameter cylindrical portion 16*b* and the inside cylindrical portion 16*c* in radial directions) is the maximum width (the width shown by W1 in FIG. 8A) at a given position, and gradually decreases in both of circumferential directions from the given position to be the minimum width (the width shown by W2 in FIG. 8A) at the opposite position to the given position in radial directions.

If a small quantity (e.g., not larger than about 30 μl) of liquid, such as a reagents is fed into the injecting section 26, the liquid is fed into one or both of the inside fluid housing chamber 30 and the outside fluid housing chamber 28. Since the capillary rise (the height of the liquid level raised by capillary force) Z is expressed by $Z=2T\cos\theta/\gamma\cdot r\cdot g$ (θ: contact angle, T: surface tension, γ: liquid density, r: capillary radius, g: gravitational acceleration), the capillary force exerted on the liquid in the outside fluid housing chamber 28, which has a smaller width in radial directions than the diameter of the inside fluid housing chamber 30, is greater than the capillary force exerted on the liquid in the inside fluid housing chamber 30. Therefore, as shown in FIGS. 9A and 9B, the most part of the liquid fed into the injecting section 26 is drawn into the outside fluid housing chamber 28 due to capillarity, and is held in the outside fluid housing chamber 28 as shown by reference number 32. Thus, the width W3 (see FIG. 8D) of each of the slits 16*b* formed in the inside cylindrical portion 16*c*, and the maximum width W1 of the annular outside fluid housing chamber 28 (the maximum distance between the outside small-diameter cylindrical portion 16*b* and the inside cylindrical portion 16*c* in radial directions) may be suitably determined so that the most part of the liquid fed into the injecting section 26 is drawn into the outside fluid housing chamber 28.

The maximum width W1 of the outside fluid housing chamber 28 is preferably not less than 1.2 times, more preferably not less than 1.5 times, as long as the minimum width of the outside fluid housing chamber 28 (the minimum distance between the outside small-diameter cylindrical portion 16*b* and the inside cylindrical portion 26*c* in radial directions). For example, when the inside diameter of the outside small-diameter cylindrical portion 16*b* is 5.2 mm and when the outside diameter of the inside cylindrical portion 16*c* is 4 mm, if the central axis of the inside cylindrical portion 16*c* is offset by 0.15 mm in a radial direction from the central axis of the outside small-diameter cylindrical portion 16*b*, the minimum width W2 of the outside fluid housing chamber 28 is 0.45 mm, and the maximum width W1 thereof is 0.75 mm, so that the maximum width W1 is about 1.67 times as long as the minimum width W2. However, the maximum width W1 is preferably not longer than about 1 mm so that the most part of the fluid fed into the injecting portion 26 is drawn into the outside fluid housing chamber 28 due to capillarity through the slits 16*d* in vicinity of the portion of the maximum width W1 of the outside fluid housing chamber 28.

Furthermore, since the inside cylindrical portion 16*c* is eccentrically arranged in radial directions with respect to the outside small-diameter portion 16*b*, the capillary force exerted on the liquid in the outside fluid housing chamber 28 varies in circumferential directions. Therefore, if a small quantity (e.g., about 30 μL) of liquid is injected into the injecting portion 26, the height of the liquid level in the outside fluid housing chamber 28 varies in circumferential directions. That is, the capillary force exerted on the liquid in the portion of the maximum width W1 of the outside fluid housing chamber 28 is weak, and the capillary force exerted on the liquid in the portion of the minimum width W2 thereof is strong. Therefore, if a small quantity of liquid is injected into the injecting portion 26, the height of the liquid level in the portion of the minimum width W2 of the outside fluid housing chamber 28 is higher than that in the portion of the maximum width W1 thereof.

After the most part of the liquid fed into the injecting section 26 is accumulated in the outside fluid housing chamber 28, if the total quantity of the liquid exceeds the volume of the outside fluid housing chamber 28 (e.g., about 30 μl) by additionally feeding the liquid into the injecting section 26, the liquid flows into the inside cylindrical portion 16*c* via the opening of the upper end of the inside cylindrical portion 16*c* and/or the slits 16*d*, so that the liquid can be filled in the outside fluid housing chamber 28 and the interior of the inside cylindrical portion 16*c* to entirely extend in the fluid handling unit 16.

Thus, according to the fluid handling unit 16 in this preferred embodiment, if a small quantity of liquid, such as a reagent, is fed into the injecting section 26, the most part of the liquid fed into the injecting section 26 is drawn into the outside fluid housing chamber 28, and flows in circumferential directions in the outside fluid housing chamber 28 to be held in the outside fluid housing chamber 28. Therefore, even if the outside fluid housing chamber 28 is used as a reaction chamber to detect a specimen by a small quantity of reagent, it is possible to greatly increase the height of the liquid level to increase the surface area of a reaction wall surface (the inner wall surface of the outside fluid housing chamber 28), and it is possible to decrease the distance between the specimen and the reaction wall surface. Thus, it is possible to improve the reaction efficiency to shorten the reaction time, and it is possible to decrease the quantity of the used reagent to reduce the costs.

According to the fluid handling unit 16 in this preferred embodiment, even if the quantity of a reagent for use in analysis is very small, the reagent can be stably held in the outside fluid housing chamber 28 serving as a reaction chamber, so that it is possible to further improve the accuracy of analysis. Moreover, if the quantity of available specimen is very small so that the concentration of the specimen in a solution containing the specimen is very low, there are some cases where conventional microwell plates can not obtain stable results of analysis since the specimen in the solution can not reach the reaction part of the wall surface of wells. However, the fluid handling unit 16 in this preferred embodiment can stably feed a specimen into the outside fluid housing chamber 28 serving as a reaction chamber to allow the specimen to easily reach the reaction wall surface, so that it is possible to further improve the accuracy of analysis in comparison with conventional microwell plates.

According to the fluid handling unit 16 in this preferred embodiment, a reagent fed into the inside fluid housing chamber 30 from the injecting section 26 is drawn into the outside fluid housing chamber 28 to be held therein even if the reagent is not fed along the inner wall of the injecting section 26 in order to feed the reagent into the outside fluid housing chamber 28. Therefore, the reagent is automatically moved into the outside fluid housing chamber 28 to be held therein regardless of the reagent feeding position, so that it is possible to easily carry out the operation for feeding the reagent.

Furthermore, if the width of each of the slits 16*d* on the side of the inside face of the inside cylindrical portion 16*c* is longer than that on the side of the outside face thereof as the fluid handling unit 16 in this preferred embodiment, even if the quantity of a liquid, such as a reagent, fed into the injecting section 26 is small (not larger than the volume of the outside fluid housing chamber 28), the variation in area of the liquid contacting the inner wall surface of the outside fluid housing chamber 28 can be suppressed between a plurality of fluid handling units 16 and between measuring operations.

According to the fluid handling unit 16 in this preferred embodiment, the upper end face of the inside cylindrical portion 16*c* is inclined inwardly downwards to form the inclined surface 16*f*. Therefore, when liquid is injected into the fluid handling unit 16 by means of a pipette chip, even if the tip portion of the pipette chip hits against the upper end of the inside cylindrical portion 16*c*, the tip portion of the pipette chip is smoothly guided into the inside fluid housing chamber 30, so that it is possible to prevent the inside cylindrical portion 16*c* from being deformed and broken by the collision with the pipette chip.

Moreover, according to the fluid handling unit 16 in this preferred embodiment, after a sufficient quantity of cleaning solution is fed into the injecting section 26 to be filled in the interior of the fluid handling unit 16 (the interiors of the injecting section 26, outside fluid housing chamber 28 and inside fluid housing chamber 30), it is possible to easily discharge the cleaning solution. Therefore, the fluid handling unit 16 in this preferred embodiment has excellent cleaning performance, and can lower background during measurement. In addition, since the height of the upper end of the inside cylindrical portion 16*c* is lower than the upper end of the outside large-diameter cylindrical portion 16*a*, a sufficient quantity of cleaning solution can be fed into the injecting section 26 to float components to be removed, so that the components can be discharged by means of a pipette or the like. Therefore, the fluid handling unit 16 in this preferred embodiment has more excellent cleaning performance than that when the height of the upper end of the inside cylindrical portion 16*c* is equal to the height of the upper end of the outside large-diameter cylindrical portion 16*a*.

In particular, according to the fluid handling unit 16 in this preferred embodiment, since the inside cylindrical portion 16*c* is eccentrically arranged in radial directions with respect to the outside small-diameter portion 16*b*, the capillary force exerted on the liquid in the outside fluid housing chamber 28 varies in circumferential directions. Therefore, if a small quantity of liquid exists in the outside fluid housing chamber 28, the height of the liquid level in the outside fluid housing chamber 28 varies in circumferential directions. That is, the capillary force exerted on the liquid in the outside fluid housing chamber 28 is weakest in the portion of the maximum width W1 of the outside fluid housing chamber 28, and gradually increases in circumferential directions of the outside fluid housing chamber 28 to be strongest in the portion of the minimum width W2 thereof. Thus, if a small quantity of liquid exists in the outside fluid housing chamber 28, the height of the liquid level in the outside fluid housing chamber 28 is lowest in the portion of the maximum width W1, and gradually increases in circumferential directions of the outside fluid housing chamber 28 to be highest in the portion of the minimum width W2. Therefore, even if a small quantity of a cleaning solution remains in the outside fluid housing chamber 28 between the outside small-diameter cylindrical portion 16*b* and the inside cylindrical portion 16*c* when the cleaning solution is discharged, the remaining cleaning solution continuously flows from the portion of the maximum width W1 toward the portion of the minimum width W2 as shown by arrow in FIG. 10, so that the height of the liquid level in the portion of the minimum width W2 is higher than that in the portion of the maximum width W1. Thus, if a pipette, a suction nozzle or the like is arranged in the vicinity of the portion of the minimum width W2, it is possible to easily and sufficiently suck the cleaning solution (while preventing part of the cleaning solution from remaining in the outside fluid housing chamber 28 by cutting the flow of the cleaning solution), so that it is possible to further improve the efficiency of cleaning while further lowering background during measurement.

Figure 11:
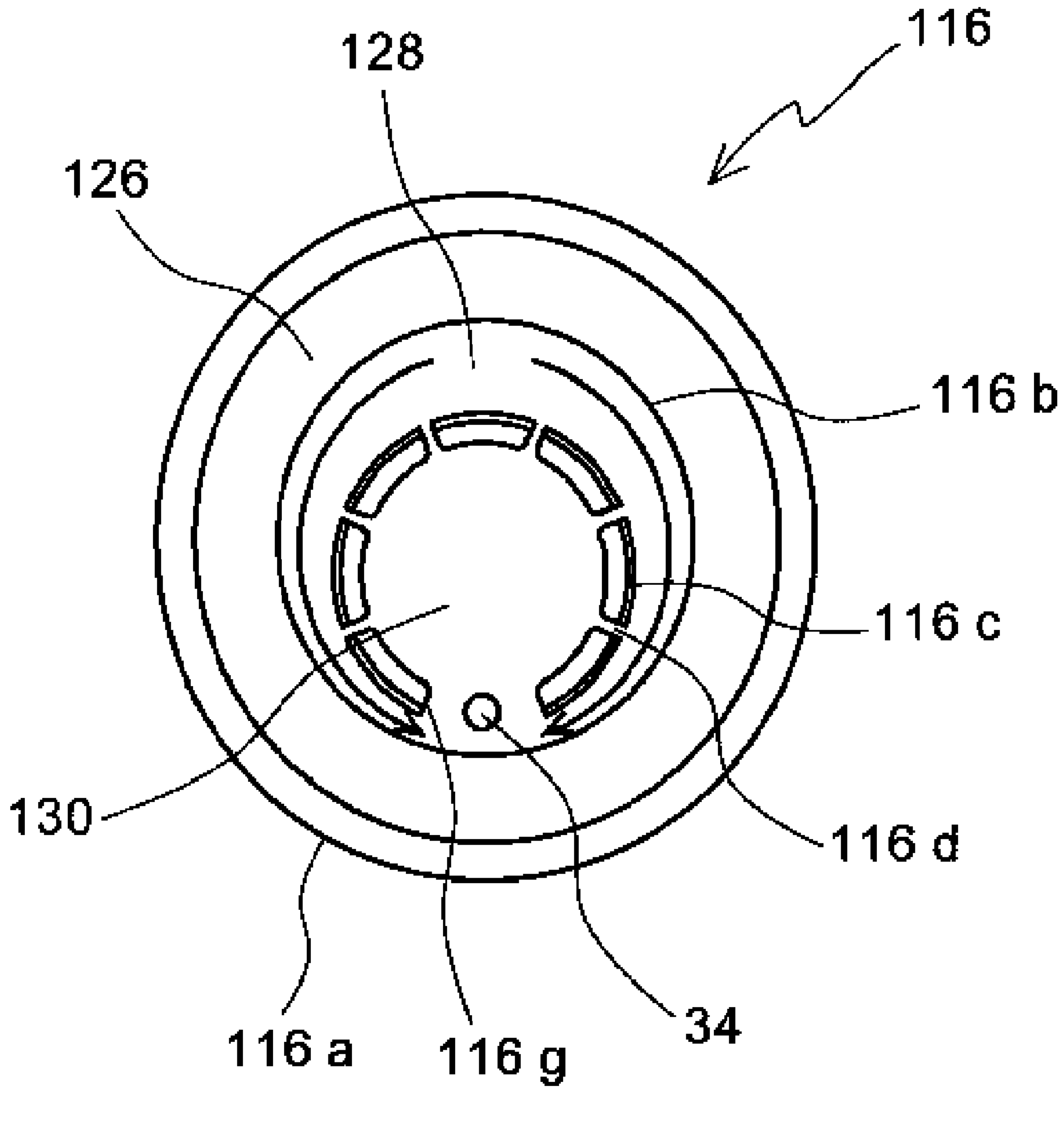
FIG. 11 is an enlarged plan view of a first modified example of the fluid handling unit shown in FIGS. 8A through 8D.

FIG. 11 shows a first modified example of a fluid handling unit 16 in this preferred embodiment. The fluid handling unit 116 in this modified example substantially has the same structure as that of the fluid handling unit 16 in the above-described preferred embodiment, except that one of the eight pillars forming the inside cylindrical portion 16*c* of the fluid handling unit 16 in the above-described preferred embodiment is not provided, the one of the eight pillars being nearest to the portion of the minimum width W2 of the outside fluid housing chamber 28, and that a nozzle housing portion 116*g* is formed in the portion of the minimum width W2. Therefore, 100 is added to the reference numbers given to the same structural portions as those of the fluid handling unit 16 to omit the duplicate descriptions thereof.

The nozzle housing portion 116*g* extends substantially linearly from the lower end to upper end of an inside cylindrical portion 116*c* substantially in parallel to slits 116*d* to pass through the inside cylindrical portion 116*c*. The nozzle housing portion 116*g* may have such a width that it can house therein a suction nozzle 34 or the like for discharging liquid in the fluid handling unit 116 to allow the suction nozzle 34 or the like to be arranged in the vicinity of the inner wall of an outside small-diameter cylindrical portion 116*b*. The width of the nozzle housing portion 116*g* is preferably shorter than about the half of the diameter of the inside cylindrical portion 116*c*. For example, when the outside diameter of the inside cylindrical portion 116*c* is 4 mm and when the width (or diameter) of the suction nozzle 34 is about 1 mm, the width of the nozzle housing portion 116*g* is preferably longer than about 1 mm and shorter than about 2 mm. If such a nozzle housing portion 116*g* is formed, the suction nozzle 34 can be arranged in the vicinity of the inner wall of the outside small-diameter cylindrical portion 116*b*. Therefore, a cleaning solution can be easily and sufficiently discharged so as to hardly remain in the interior of the fluid handling unit 116 (the interiors of an injecting section 126, outside fluid housing chamber 128 and inside fluid housing chamber 130), so that it is possible to further improve cleaning performance in comparison with the fluid handling unit 16 in the above-described preferred embodiment.

Figure 12:
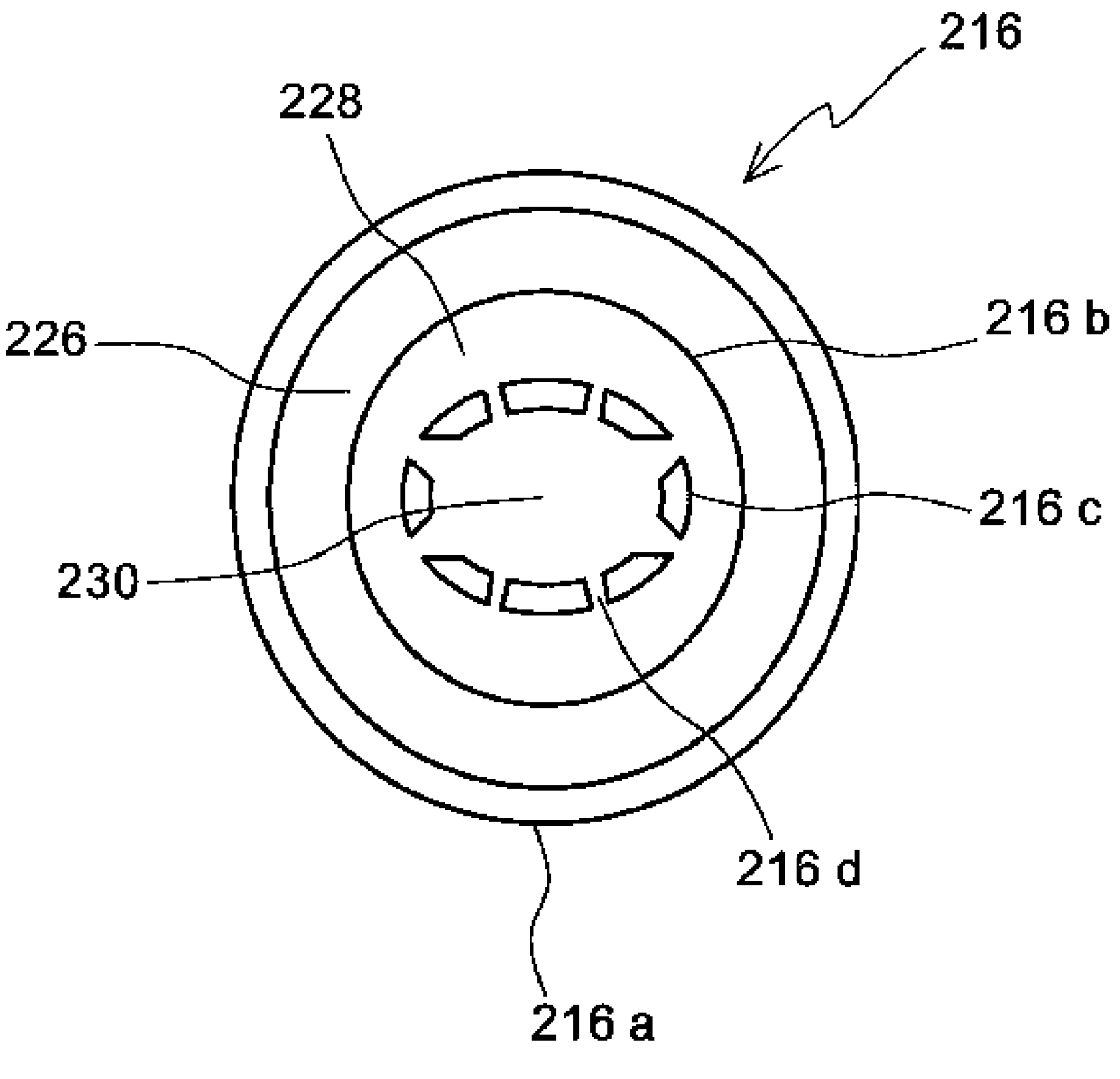
FIG. 12 is an enlarged plan view of a second modified example of the fluid handling unit shown in FIGS. 8A through 8D.

FIG. 12 shows a second modified example of a fluid handling unit 16 in this preferred embodiment. The fluid handling unit 216 in this modified example substantially has the same structure as that of the fluid handling unit 16 in the above-described preferred embodiment, except that an elliptic cylindrical portion 216*c* is provided in place of the inside cylindrical portion 16*c* of the fluid handling unit 16 in the above-described preferred embodiment. Therefore, 200 is added to the reference numbers given to the same structural portions as those of the fluid handling unit 16 to omit the duplicate descriptions thereof.

The elliptic cylindrical portion 216*c* is a substantially elliptic cylindrical portion which extends upwards in the same axial directions as those of an outside small-diameter cylindrical portion 216*b* from the upper face of the bottom face portion of the outside small-diameter cylindrical portion 216*b*. That is, the central axis of the elliptic cylindrical portion 216*c* (the axis passing through the intersection point of the major and minor axes of an elliptic section and extending in parallel to the elliptic cylindrical portion 216*c*) is the same as the central axis of the outside small-diameter cylindrical portion 216*b*. The height of the upper end of the elliptic cylindrical portion 216*c* is lower than the height of the upper portion of the outside small-diameter cylindrical portion 216*b*. The elliptic cylindrical portion 216*c* has a plurality of slits 216*d* (eight slits 216*d* in this preferred embodiment) which extend substantially linearly in substantially parallel to each other from the lower end to upper end of the elliptic cylindrical portion 216*c*. The plurality of slits 216*d* pass through the elliptic cylindrical portion 216*c*, and are arranged at regular intervals. That is, the elliptic cylindrical portion 216*c* comprises eight pillars which are spaced from each other so as to form the eight slits 216*d*. The width of each of the slits 216*d* is a few micrometers to hundreds micrometers, and the width of each of the slits 216*d* on the side of the inside face of the elliptic cylindrical portion 216*c* is longer than that on the side of the outside face thereof. If such an elliptic cylindrical portion 216*c* is provided, the width of an outside fluid housing chamber 228 in radial directions is the maximum width in the directions of the minor axis of the elliptic section of the elliptic cylindrical portion 216*c*, and gradually decreases in both of circumferential directions to be the minimum width in the directions of the major axis of the elliptic section thereof, so that it is possible to obtain the same effects as those in the above-described preferred embodiment.

Figure 13:
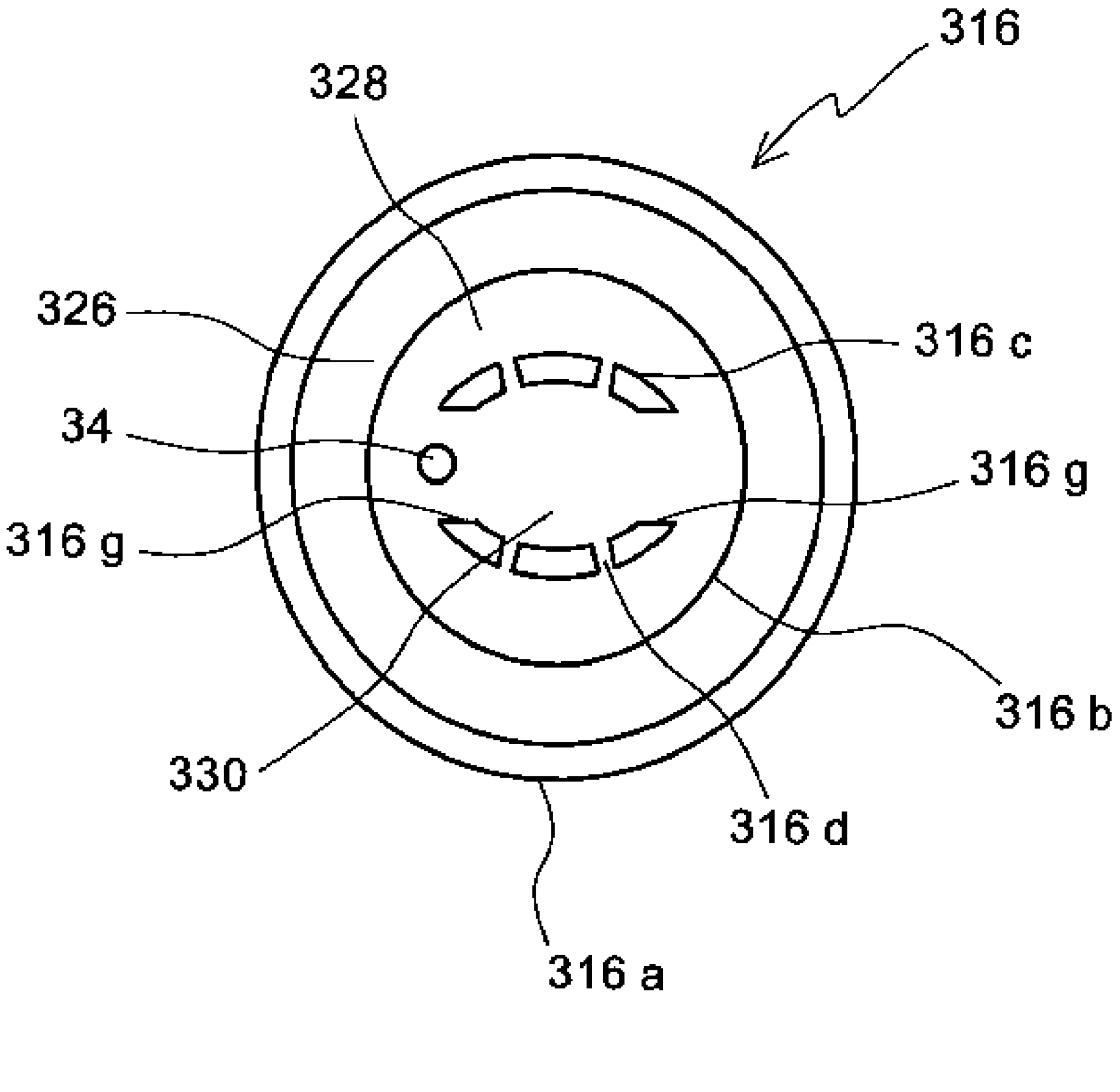
FIG. 13 is an enlarged plan view of a third modified example of the fluid handling unit shown in FIGS. 8A through 8D.

FIG. 13 shows a third modified example of a fluid handling unit 16 in this preferred embodiment. The fluid handling unit 316 in this modified example substantially has the same structure as that of the fluid handling unit 216 in the above-described second modified example, except that two of the eight pillars forming the elliptic cylindrical portion 216*c* of the fluid handling unit 216 in the above-described second modified example are not provided, the two of the eight pillars being nearest to the portions of the minimum width of the outside fluid housing chamber 228 (the portions on both sides in the major axis of the elliptic section), and that nozzle housing portions 316*g* are formed in the portions of the minimum width. Therefore, 100 is further added to the reference numbers given to the same structural portions as those of the fluid handling unit 216 to omit the duplicate descriptions thereof.

Each of the nozzle housing portions 316*g* extends substantially linearly from the lower end to upper end of an elliptic cylindrical portion 316*c* substantially in parallel to slits 316*d* to pass through the elliptic cylindrical portion 316*c*. Each of the nozzle housing portions 316*g* may have such a width that it can house therein a suction nozzle 34 or the like for discharging liquid in the fluid handling unit 316 to allow the suction nozzle 34 or the like to be arranged in the vicinity of the inner wall of an outside small-diameter cylindrical portion 316*b*. The width of each of the nozzle housing portions 316*g* is preferably shorter than about the half of the major axis of the elliptic section of the elliptic cylindrical portion 316*c*. If such nozzle housing portions 116*g* are formed, the suction nozzle 34 can be arranged in the vicinity of the inner wall of the outside small-diameter cylindrical portion 316*b*. Therefore, a cleaning solution can be easily and sufficiently discharged so as to hardly remain in the interior of the fluid handling unit 316 (the interiors of an injecting section 326, outside fluid housing chamber 328 and inside fluid housing chamber 330), so that it is possible to further improve cleaning performance in comparison with the fluid handling unit 216 in the above-described second modified example.

Figure 14:
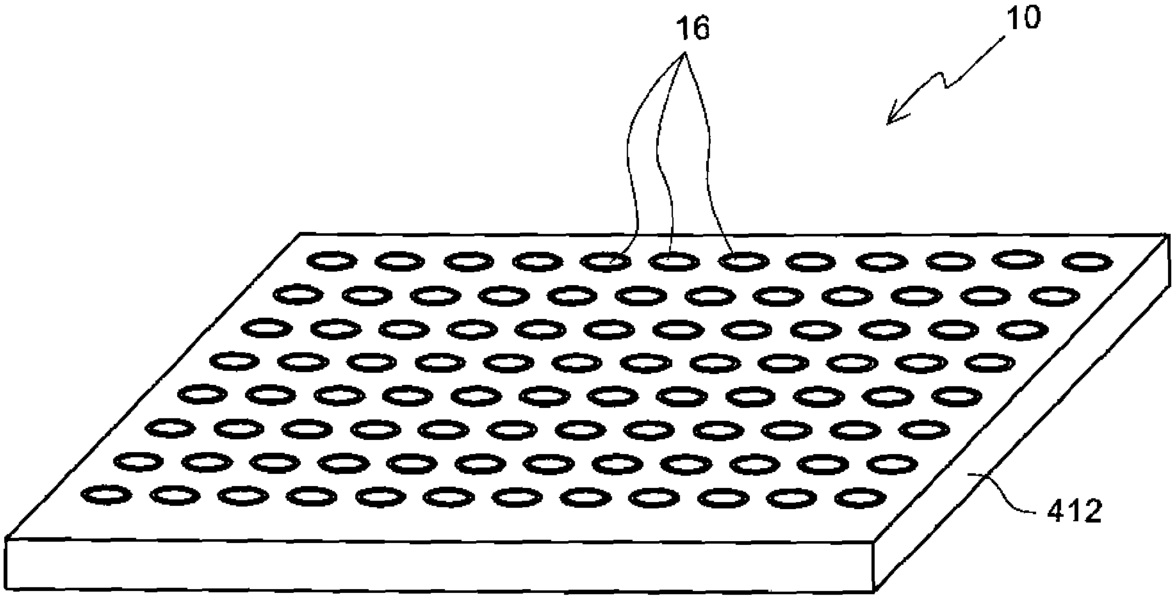
FIG. 14 is a perspective view of a modified example of a fluid handling apparatus according to the present invention.

Furthermore, since each of the fluid handling unit 16 in this preferred embodiment and the fluid handling units 116, 216 and 316 in the first through third modified examples can be integral-molded by injection molding or the like, so that they can be easily produced. As a modified example of the fluid handling apparatus 10 in this preferred embodiment, the plurality of fluid handling units 16, 116, 216 or 316 arranged on the supporting member 13 at regular intervals in a row maybe integral-molded by injection molding or the like. Alternatively, as shown in FIG. 14, the plurality of fluid handling units 16, 116, 216 or 316 arranged on a plate-like apparatus body 412 at a matrix may be integral-molded by injection molding or the like without providing any fluid handling unit supporting members.

The surface area of the reaction surface may be increased to enhance the sensitivity of measurement by forming fine irregularities on the inner wall surface (reaction surface) of any one of the outside fluid housing chambers 28, 128, 228 and 328 capable of being used as a reaction chamber of the fluid handling unit 16 in this preferred embodiment and the fluid handling units 116, 216 and 316 in the first through third modified examples. In addition, the reaction surface having such fine irregularities may be treated with a surface treating agent (a coupling agent) Such a surface treating agent is preferably a compound having a functional groove capable of applying hydrophilic property to the reaction surface, in order to fluidize a solution containing a biosubstance, such as a protein, on the reaction surface to uniformly fix the biosubstance on the reaction surface. Such a functional group may be selected from the group consisting of hydroxyl, amino, carboxyl, aldehyde, epoxy, thiol, chloro, bromo, iodine, cyano and isothiocyanate groups. For example, when the fluid handling unit 16 is made of polycarbonate (PC), a surface treating layer (a coupling layer) of polysilazane or the like may be formed on the reaction surface having fine irregularities of the outside fluid housing chamber 28, 128, 228 or 328.

When any one of the fluid handing unit 16 in this preferred embodiment and the fluid handling units 116, 217 and 316 in the first through third modified examples is made of a resin material, the inner wall surface (reaction surface) of the outside fluid housing chamber 28 capable of being used as a reaction chamber may be treated with a coupling agent to be reformed, so that a protein can be densely immobilized on the reaction surface. Before the treatment with such a coupling agent is carried out, a layer of a metal compound or coating containing oxygen atoms on the reaction surface maybe formed. For example, after a silica coating is applied on the inner wall surface (reaction surface) of any one of the outside fluid housing chambers 28, 128, 228 and 328 of the fluid handling units 16, 116, 216 and 316 of a resin, the surface may be treated with a silane coupling agent, such as aminopropyl trimethoxysilane.

As an example of a fluid handling unit 16 in this preferred embodiment, an example of a fluid handling unit used as a sample analyzing unit will be described below.

First, 100 μl of anti-TNF-α antibody (M303) diluted with 5 μg/ml of a reagent adjusting diluting buffer (50 ml of phosphoric acid buffer) was fed into the injecting portion 26 of the fluid handling unit 16 to be held at 25° C. for ten minutes to immobilize a capturing (or catching) antibody on the inner wall of the fluid handling unit 16. Thereafter, 250 μl of a cleaning solution (PBS-0.02% Tween 20) was fed into the injecting section 26, and then, discharged to clean the interior of the fluid handling unit 16 three times.

Then, after 220 μl of a blocking solution (PBS-3% BSA) was fed into the injecting section 26 to be held at 4° C. for 16 hours to block the inner wall of the fluid handling unit 16, and then, the blocking solution was discharged.

Then, 100 μl of TNF-α antibody (S-TFNA) diluted with 5 to 200 pg/ml of a reagent adjusting diluting buffer (PBS-3% BSA) was fed into the injecting section 26 to be held at 25° C. for one hour to cause an antigen reaction (specimen reaction). Thereafter, 200 μl of a cleaning solution (PBS-0.02% Tween 20) was fed into the injecting section 26, and then, discharged to clean the interior of the fluid handling unit 16 three times.

Then, 100 μl of a biotin labeled antibody (an antibody labeled with biotin) (M302B) diluted with 0.5 μg/ml of a reagent adjusting diluting buffer (PBS-3% BSA) was fed into the injecting section 26 to be held at 25° C. for one hour to cause a detecting antibody reaction. Thereafter, 250 μl of a cleaning solution (PBS-0.02% Tween 20) was fed into the injecting section 26, and then, discharged to clean the interior of the fluid handling unit 16 three times.

Then, 100 μl of an enzyme (HRP Peroxidase Streptavidin (SA-5004)) diluted with a reagent adjusting diluting buffer (PBS-3% BSA) was fed into the injecting section 26 to be held at 25° C. for twenty minutes to cause an enzyme reaction. Thereafter, 250 μl of a cleaning solution (PBS-0.02% Tween 20) was fed into the injecting section 26, and then, discharged to clean the interior of the fluid handling unit 16 three times.

Then, 100 μl of a substrate (TMB) was fed into the injecting section 26 to be held at 25° C. for ten minutes to cause a substrate reaction, and then, 100 μl of a reaction stop solution (1N HCl) was fed into the injecting section 26 to stop the reaction. Then, the inside fluid housing chamber 30 was irradiated with light having a wavelength of 450 nm in a longitudinal direction (in a vertical direction) to measure the intensity of absorbance of a reaction solution in the inside fluid housing chamber 30.

As a comparative example, a substantially cylindrical well having the same shape as that of the mounting recessed portion 14 of the fluid handling apparatus 10 in this preferred embodiment was used for carrying out the same measurement.

As a result, it was found that the absorbance in Example, in which the fluid handling unit 16 in this preferred embodiment is used, is twice or more of that in Comparative Example. Thus, it is possible to greatly enhance the intensity of measurement even if the quantity of liquid (the quantity of a capturing (or catching) antibody, an antigen serving as a specimen, a detecting antibody or the like) is substantially equal to that in Comparative Example, and it is possible to obtain the intensity of measurement, which is substantially equal to that in Comparative Example, even if the quantity of liquid is far smaller than that in Comparative Example. It was also found that it is possible to allow the cleaning solution to hardly remain in the fluid handling unit 16, so that it is possible to lower background.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A fluid handling unit comprising:

an container body having an opening at an upper end thereof, a bottom portion at a lower end thereof, and a side portion which extends from a peripheral portion of an upper face of the bottom portion, said container body defining therein a fluid housing section by the bottom portion and the side portion;

a partition wall portion which extends from the bottom portion of the container body and which extends along the side portion of the container body, said partition wall portion dividing the fluid housing section of the container body into an inside fluid housing chamber and an outside fluid housing chamber which surrounds the inside fluid housing chamber; and at least one communication passage which passes through the partition wall portion to establish a communication between the inside fluid housing chamber and the outside fluid housing chamber, wherein a distance between the side portion of the container body and the partition wall portion varies in circumferential directions for changing a capillary force, which is exerted on a liquid housed in the outside fluid housing chamber, in the circumferential directions which extend along the peripheral portion of the upper face of the bottom portion of the container body.

2. A fluid handling unit as set forth in claim 1, wherein said distance between the side portion of the container body and the partition wall portion gradually varies in the circumferential directions so that the liquid housed in the outside fluid housing chamber flows in the circumferential directions by the capillary force.

3. A fluid handling unit as set forth in claim 1, wherein said liquid housed in the outside fluid housing chamber flows in the circumferential directions by the capillary force from a wider portion, in which the distance between the side portion of the container body and the partition wall portion is wider, toward a narrower portion in which the distance between the side portion of the container body and the partition wall portion is narrower.

4. A fluid handling unit as set forth in claim 1, wherein said distance between the side portion of the container body and the partition wall portion is substantially uniform in a direction vertically perpendicular to the circumferential directions.

5. A fluid handling unit as set forth in claim 1, wherein said side portion of the container body has a substantially cylindrical inside face, and said partition wall portion has a substantially cylindrical outside face which is eccentrically arranged in radial directions with respect to the inner face of the side portion of the container body.

6. A fluid handling unit as set forth in claim 1, wherein said side portion of the container body has a substantially cylindrical inside faces and said partition wall portion has a substantially elliptic cylindrical outside face.

7. A fluid handling unit as set forth in claim 1, wherein said communication passage comprises a plurality of slits which pass through the partition wall portion and which extend from a lower end of the partition wall portion to an upper end thereof.

8. A fluid handling unit as set forth in claim 7, wherein said plurality of slits are arranged at regular intervals in the circumferential directions.

9. A fluid handling unit as set forth in claim 7, wherein said plurality of slits are arranged substantially in parallel, and a nozzle housing portion is formed so as to pass through the partition wall portion to extend substantially in parallel to the plurality of slits from the lower end of the partition wall portion to the upper end thereof, said nozzle housing portion being capable of housing therein a suction nozzle for sucking a fluid flowing in the circumferential directions into a narrower portion, in which the distance between the side portion of the container body and the partition wall portion is narrower, from a wider portion in which the distance between the side portion of the container body and the partition wall portion is wider.

10. A fluid handling unit as set forth in claim 1, wherein a liquid in the inside fluid housing chamber is caused to enter the outside fluid housing chamber due to capillarity while being prevented from entering the inside fluid housing chamber when the quantity of the liquid fed into the fluid housing section from the opening of the container body is not larger than a predetermined quantity, and the liquid in the outside fluid housing chamber is allowed to enter the inside fluid housing chamber when the quantity of the liquid fed to the fluid housing section from the opening of the container body exceeds the predetermined quantity.

11. A fluid handling unit as set forth in claim 10, wherein the most part of the liquid in the inside fluid housing chamber enters the outside fluid housing chamber when the quantity of the liquid fed into the fluid housing section from the opening of the container body is not larger than the predetermined quantity.

12. A fluid handling unit as set forth in claim 1, wherein said communication passage causes the liquid in the inside fluid housing chamber to enter the outside fluid housing chamber while preventing the liquid in the outside fluid housing chamber from entering the inside fluid housing chamber, by a difference between a capillary force exerted in the inside fluid housing chamber and a capillary force exerted in the outside fluid housing chamber, when the quantity of the liquid fed into the fluid housing section from the opening of the container body is not larger than a predetermined quantity.

13. A fluid handling unit as set forth in claim 12, wherein said capillary force exerted in the outside fluid housing chamber is greater than said capillary force exerted in the inside fluid housing chamber.

14. A fluid handling unit as set forth in claim 1, wherein said partition wall portion has a height which is lower than that of the side portion of the container body.

15. A fluid handling unit as set forth in claim 1, wherein said bottom portion of the outside fluid housing chamber is inclined downwards as a distance from the inside fluid housing chamber decreases.

16. A fluid handling unit as set forth in claim 1, wherein the height of the lowest portion of the bottom portion of the outside fluid housing chamber is substantially equal to the height of the bottom portion of the inside fluid housing chamber.

17. A fluid handling unit as set forth in claim 1, wherein the width of each of said slits on the side of the inside fluid housing chamber is longer than that on the side of the outside fluid housing chamber.

18. A fluid handling unit as set forth in claim 1, wherein said fluid handling unit is integral-molded.

19. A fluid handling apparatus comprising:

an apparatus body; and a plurality of fluid handling units arranged on said apparatus body, wherein each of said plurality of fluid handling units is a fluid handling unit as set forth in claim 1.

20. A fluid handling apparatus as set forth in claim 19, wherein said plurality of fluid handling units are arranged on said apparatus body as a matrix.

21. A fluid handling apparatus as set forth in claim 19, wherein said plurality of fluid handling units, together with said apparatus body, are integral-molded.

22. A fluid handling apparatus as set forth in claim 19, wherein said apparatus body comprises a frame and a plurality of supporting members arranged on the frame substantially in parallel, and said plurality of fluid handling units are arranged on each of said supporting members at regular intervals in a row.

23. A fluid handling apparatus as set forth in claim 22, wherein said plurality of fluid handling units, together with each of said supporting member, are integral-molded.

* * * * *